US008071304B2

(12) United States Patent
Brant et al.

(10) Patent No.: US 8,071,304 B2
(45) Date of Patent: Dec. 6, 2011

(54) METHODS FOR DETECTING A POLYMORPHISM IN THE NFKB1 GENE PROMOTER

(75) Inventors: Steven R. Brant, Reisterstown, MD (US); Amir Karban, Baltimore, MD (US); Franklin Nouvet, Laurel, MD (US); Theodore M. Bayless, Baltimore, MD (US); James J. Potter, Baltimore, MD (US); Esteban Mezey, Baltimore, MD (US); Toshihiko Okazaki, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 620 days.

(21) Appl. No.: 10/818,037

(22) Filed: Apr. 5, 2004

(65) Prior Publication Data

US 2006/0141478 A1    Jun. 29, 2006

Related U.S. Application Data

(60) Provisional application No. 60/460,438, filed on Apr. 5, 2003.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ...... 435/6.11; 435/6.1; 435/6.12; 435/6.17; 435/91.2; 536/24.1; 536/24.31; 536/24.33

(58) Field of Classification Search .......... None
See application file for complete search history.

(56) References Cited

U.S. PATENT DOCUMENTS 5,324,631 A * 6/1994 Helentjaris et al. ............... 435/6

OTHER PUBLICATIONS

Oliver et al. Inflammatory Bowel Disease. 2005. 11: 576-579.*
Orozco et al. Tissue Antigens. 2005. 65: 183-186.*
Rueda et al. Scandinavian Journal of Gastroenterology. 2006. 41: 420-423.*
Riemann et al. Pharmacogenetics and Genomics. 2006. 16: 783-788.*
Glas et al. Inflammatory Bowel Disease. 2006. 12: 606-611.*
Szamosi et al. Dig Dis Sci. 2009. 54: 351-359.*
Cogswell et al. Journal Immunology. 1993. 150: 2794-2804.*
Ten et al. The EMBO J. (1992) 11: 195-203.*
Strausberg, R. NCBI Database, National Library of Medicine (Bethesda, MD, USA). GenBank Accession No. BM919824, Mar. 2002.*
Karbin et al. Human Molecular Genetics. Nov. 12, 2003. 13: 35-43.*
Brant et al. Digestive Disease Week Abstracts and Itinerary Planner. May 17-22, 2003, abstract No. M1537.*
Chang et al. GenBank Accession No. AF213884S1, Feb. 2000.*
Mirza et al. Gut. 2005. 54:1205-1206.*

* cited by examiner

*Primary Examiner* — Carla Myers
(74) *Attorney, Agent, or Firm* — Edwards Wildman Palmer LLP; Peter F. Corless; Melissa Hunter-Ensor, Esq.

(57) ABSTRACT

The present invention discloses a functional relationship between a recognized disease condition and a polymorphism in the nucleotide factor kappa B promoter (NFKB1). This relationship provides a platform for methods of altering promoter activity and for determining similar relationships between specific pathologies and identified polymorphisms. A statistically significant risk of developing ulcerative colitis was shown to be correlated with the presence of an ATTG insertion/deletion in the NFKB1 promoter and is likely to apply also to a variety of other inflammatory diseases.

4 Claims, 9 Drawing Sheets

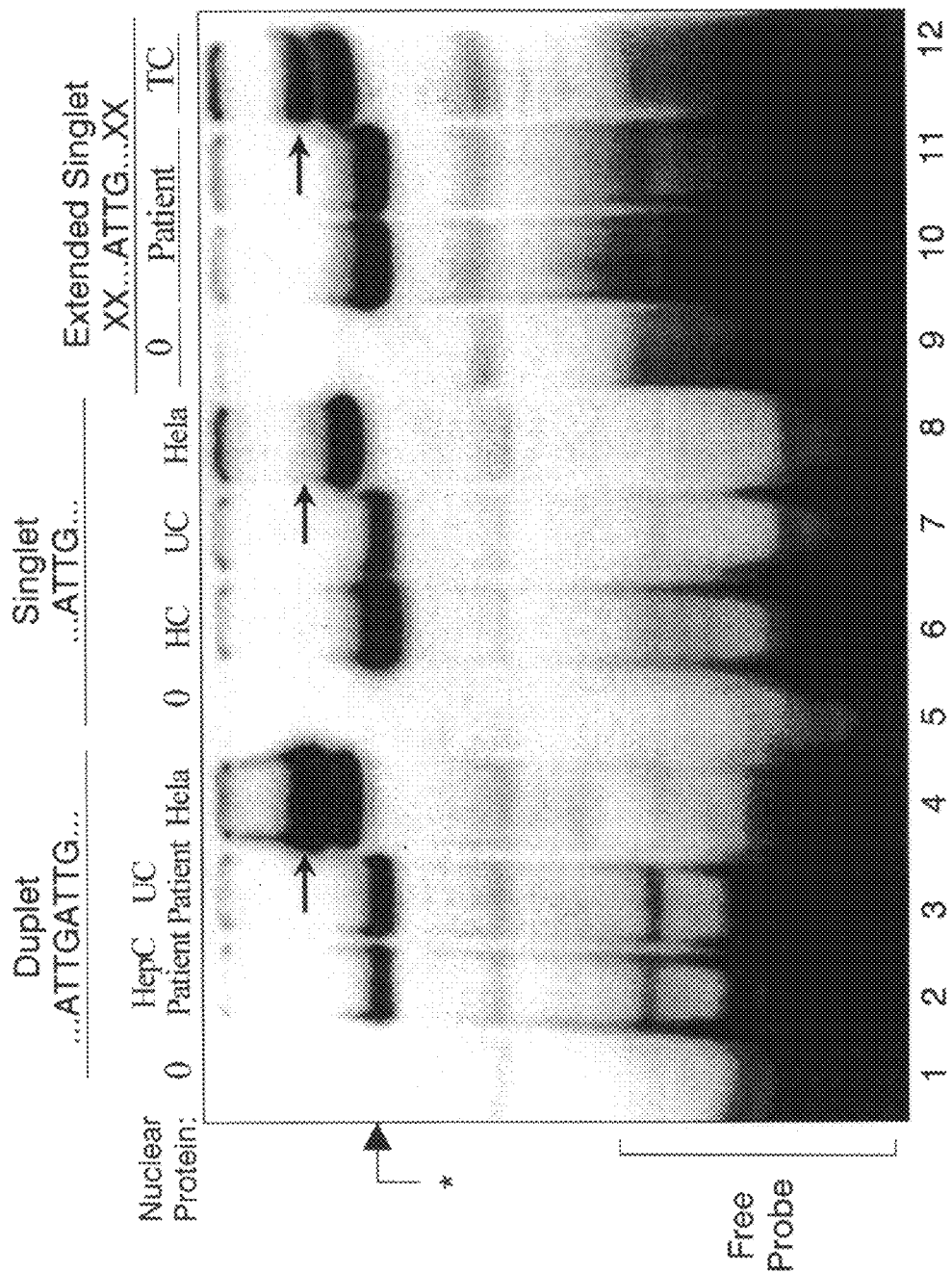

METHODS FOR DETECTING A POLYMORPHISM IN THE NFKB1 GENE PROMOTER

RELATED APPLICATIONS

This application claims benefit of United States Provisional Patent Application Ser. No. 60/460,438 filed Apr. 5, 2003, the entire contents of which are incorporated herein by reference.

This invention was supported in part by a grant from the National Institutes of Health DK58189. The United States Government has rights in the invention.

BACKGROUND OF THE INVENTION

1. Field of the Invention

The field of the invention relates to nucleotide factor kappa B promoter and to methods of controlling its activity in connection with a wide range of diseases. The invention provides methods of treating these diseases and provides protocols for identifying individuals who are susceptible to or at increased risk for an adverse response to stress, injury or infection. In particular, the invention relates to inflammatory diseases and to identification of at risk individuals who exhibit a singular polymorphism in the nucleotide factor kappa-B (NFKB) promoter. The polymorphism is functionally related to a high risk of disease.

2. Background

Nuclear Factor-kB

NF-kB transcription factors play an important role in regulating basic cellular functions. Abnormal NF-kB activities have been implicated in numerous disease states such as cancers, AIDS, autoimmunity and neurodegenerative diseases. Studies in mice indicate that lack of both p50 and p105 caused by deletion of the nfkb1 gene does not interfere with normal development but does alter normal immune response to pathological infections (Lin and Kobayashi, 2003).

Nuclear Factor-kB is a major transcription regulator of immune response, apoptosis and cell-growth control genes and is also an important mediator of the chronic inflammation associated with a wide range of diseases and pathological conditions, including cancer, infection, response to biological stressors and, particularly, autoimmune diseases (Baldwin, 2001). Inflammatory Bowel disease (IBD) in particular is thought to be associated with NFKB (Schreiber, 1998). IBD includes Crohn's Disease (CD) and ulcerative colitis (UC).

NF-κB is involved in the expression of several cytokines and adhesion molecules. Cytokines, for example, are produced by immune cells, and some induce proliferation and differentiation of specific cells while others induce an acute phase response in inflammation. Inflammation may be induced by acute phase response proteins such as angiotensinogen, serum amyloid protein, a1 acid glycoprotein, C3 complement or complement factor B. There is thus an important role of NF-κB modulating cytokine expression at the gene level.

NF-κB is thought to be involved in a wide variety of human diseases, including atherosclerosis, asthma, arthritis, cachexia, cancer, diabetes, euthyroid sick syndrome, AIDS, inflammatory bowel disease and stroke.

In most cells before stimulation, NF-κB primarily resides in the cytoplasm in inactive complexes through association with a sequestering inhibitory protein, termed IκB. A wide range of stimuli, including bacterial and viral products, cytokines and oxidant-free radicals, activate NF-κB. These stimuli promote NF-κB nuclear translocation by a mechanism that involves IκB phosphorylation and the ubiquitin-proteosome pathway. This phosphorylation appears to target IκB for degradation and leads to its dissociation from the NF-κB complex and subsequent translocation of NF-κB to the nucleus. There, active NF-κB binds to genomic DNA at promoter regions and thereby regulates gene transcription.

Inappropriate activation of NF-κB has been implicated in inflammation associated with a variety of human diseases and pathologic conditions, among them asthma, inflammatory arthritis, septic shock, lung fibrosis, diabetes, cancer, AIDS, atherosclerosis, stroke and IBD (Baldwin, 2001). Furthermore, several anti-inflammatory and anti-cancer drugs work in part through inhibition of NF-κB activation. For example, aspirin and glucocorticoids inhibit NF-κB (15,16). Consistent with NF-κB regulation of genes involved in the immune and inflammatory responses, mice null for several of the NF-κB subunits show defects in clearing bacterial infection along with defects in B-cell and T-cell functions.

NF-κB is thought to play a central pathogenic role in chronic intestinal inflammation. Activated NF-κB was increased and found localized to the macrophages and epithelial cells in the inflamed intestinal mucosa of CD and UC patients using immunohistochemistry methods. Schreiber et al. (1998) have found that CD and UC patients have increased NF-κB activity in intestinal lamina propria cells. Additionally, the therapeutic properties of mesalazine and sulfasalazine (the most common specific medical therapies for mild to moderate UC) rely in part on inhibition of NF-κB activation. Three CD associated mutations in the NOD2/CARD 15 gene on chromosome 16 all have a defect in their ability to activate NF-κB. This may cause a defect in the innate immune system's ability to protect the gut against invasive bacteria (Hisamatsu, Suzuki et al., 2003).

Inflammatory Bowel Diseases

Ulcerative colitis (UC) and Crohn's disease (CD) are idiopathic, chronic, frequently disabling, inflammatory bowel diseases (IBD). UC is characterized by mucosal inflammation limited to the colon, always involving the rectum and a variable extent of the more proximal colon in a continuous manner. CD inflammation is transmural, most often discontinuous and may involve any portion of the gastrointestinal tract but most commonly involves the distal ileum. The prevalence of IBD in the United States is 200-300/100,000 with a similar prevalence for UC and CD. IBD is considered a complex genetic disorder involving multiple genes of relatively low penetrance, since the familial patterns of inheritance do not conform to simple Mendelian models. Overall, 10-20% of individuals with IBD report one or more relatives with IBD. Relatives of CD patients have a 10-fold risk of developing CD and relatives of UC patients have an 8-fold risk of developing UC. However, these diseases appear to be genetically related, as relatives of CD patients have a 4-fold risk of developing UC and relatives of UC patients have a 2-fold risk of developing CD.

Ulcerative Colitis (UC)

A genetic contribution to the pathogenesis of UC has remained largely unclear. While genome-wide searches have identified several loci in linkage with the disease, case-control studies have only shown a reproducible association between UC and HLA class II genes, especially DRB1*0103 and DRB1*15 (Brant, Okazaki, 2003). Most studies have focused on HLA class II genes, although there is an increasing interest in the role of cytokines in UC pathogenesis and on the polymorphic genes that may influence cytokine secretion.

NFKB Gene

NFKB1 may be the first of perhaps several modest polymorphic risk genes that are involved with inflammation pathways associated with UC. Other cytokine regulators of the pathway that have been shown to have functional polymorphisms, and that ultimately NF-κB protein activation, include interleukin 1 receptor antagonist (IL1RN) and IκB-like gene (NFKBIL1). There is conflicting evidence for an association of allele 2 of IL1RN, the gene that encodes the interleukin 1 receptor antagonist and preliminary evidence of an association of NFKBIL1 with UC (De la Concha, Femandez-Arquero, et al., 2000). An association of the TNF(−857C) promoter polymorphism with IBD (both CD and UC) has also been reported (van Heel, et al., 2002).

NFKB1 gene, located at chromosome 4q24 is an important candidate gene for inflammatory bowel disease. The encoded Nuclear Factor-κB (NF-κB) proteins are a family of transcription factors that regulate various biological defense processes, most notably innate and adaptive immune responses, acute phase reaction and apoptosis. There are five members of the NF-κB family in mammals: p50/p105, p65/RelA, c-Rel, RelB and p52/p100. Although many dimeric forms of NF-κB have been detected, the major form of NF-κB is a heterodimer of the p50 and p65/RelA subunits, encoded by the genes NFKB1 and NFKB3, respectively. Human NFKB1 encodes two proteins, a 105 kDa, non DNA-binding, cytoplasmic molecule (p105), and a 50 kDa DNA-binding protein (p50) that corresponds to the N-terminus of p105. The NFKB1 gene spans 156 kb and has 24 exons with introns varying between 40 000 and 323 bp in length (FIG. 1).

NFKB1 has also been implicated in numerous inflammatory diseases and risk factors for immune-mediated conditions. An association has been reported between an NFKB1 microsatellite and type I diabetes in one instance. No associations have been found with NFKB1 and the exon 12+77C>T polymorphism for multiple sclerosis or Parkinson's disease (Wintermeyer, Riess, et al., 2002). LD is likely incomplete between the exon 12 SNP and the disclosed −94del/insATTG polymorphism. No functional NFKB1 genetic polymorphisms other than the −94del/insATTG have been described.

Deficiencies in the Art

There is a distinct need to identify and understand the role of genetic factors in the development of human disease, and to identify and treat those at risk for disease. Unfortunately, for many conditions, early detection is not possible so that early stage intervention and treatment opportunities are not available. Identification of a direct functional relation between atypical gene nucleotide sequences in polymorphic promoters and abnormal biological function as manifested in various diseases has yet to be established. Determination and location of the polymorphisms will allow development of diagnostic probes for clinical disorders.

Establishment of a functional relation between a promoter gene polymorphism and a pathology would provide new opportunities for intervention at the most basic stage of disease development. Interventions could be developed based on gene therapies, on alteration of transcription factors or on modification of identified nuclear binding proteins. Clearly, it would be desirable to control abnormal gene function at the gene level rather than far downstream in a damaging cascade of intertwined metabolic cycles.

SUMMARY OF THE INVENTION

The present invention addresses several issues that pertain to the understanding of the relationship between genetic polymorphisms and human disease. It will now be possible to develop treatment for pathologies associated with identified polymorphisms and, importantly, to understand where and how to detect polymorphisms that directly affect development of such pathologies.

As used herein, it is understood that the "wildtype" NFKB1 promoter is defined as the published sequence (SEQ ID NO:1) and shown in FIG. 1. It has a polymorphic repeat ATTG sequence referred to as either a duplet or a doublet. The polymorphism repeat sequence is interchangeably referred to as (1) Wildtype allele; (2) ATTG duplet; (3) allele W; or (4) −94insATTG. The polymorphism is found at position −94 (FIG. 1).

The inventors have found a singlet ATTG polymorphism that is functionally related to a disease condition. This polymorphism is variously referred to as: (1) Allele D; (2) deletion allele; −94delATTG; and (4) ATTG singlet. The polymorphism is a variant at position −94 (see FIG. 1) and differs from wildtype in that the indicated nucleotides at position −94 have been deleted and the ATTG bases inserted. The insertion may be referred to as a −94ins/delATTG.

The inventors have discovered a NFKB1 promoter polymorphism that results in altered promoter activity. The inventors have directly linked a specific polymorphism in this promoter to a well-characterized disease, making this the first demonstration of a functionally related polymorphism in the human NFKB1 promoter. Significantly, NFKB1 promoter activity is associated with a wide spectrum of human diseases and is considered a veritable linchpin in the biological cascades that are involved in such conditions as inflammation and cell death (apoptosis).

In one aspect of the invention, a functional change in the NFKB1 protein has been highly correlated with one form of inflammatory bowel disease, particularly with ulcerative colitis. Identification of an ATTG polymorphism now provides the basis for the identification of individuals at risk for developing, or in early stages of undetected, ulcerative colitis. This is the first instance of an inheritable genetic trait that is associated with a polymorphism in the NFKB1 promoter.

A four-base pair ATTG insertion/deletion polymorphism has been identified in the human NFKB1 promoter sequence. The NFKB1 gene encodes human nuclear factor-Kappa B (NFkB) protein, that exists as either of two subunits, the p105 subunit and the p50 subunits. The insertion polymorphism results in two ATTG sequences in tandem (doublet) compared to only one (singlet) found in the published reference sequence. Individuals with only singlet ATTG sequence are at greater risk for developing ulcerative colitis than those with a duplet insertion.

Oligonucleotides were designed that matched either the ATTG deletion or insertion alleles of the −94del/insATTG polymorphism (FIG. 1). Therefore, these oligonucleotides contained either a single ATTG sequence or the ATTG duplet sequence and the 6 nucleotides of the promoter immediately 5' and the 6 nucleotides immediately 3' of the ATTG singlet or doublet. Additionally, 5' and 3' overhang sequences were added to radioactively label the oligomer. Thus the oligonucleotides were identical except for having either one or two ATTG sequences in tandem in the center of each oligonucleotide.

The duplet double-stranded oligonucleotide-bound mammalian nuclear proteins, from rat and humans were as determined by electrophoretic shift assays (EMSA). Nuclear protein binding to the duplet oligonucleotide was inhibited in a dose dependent manner by an NF-kappaB1 consensus oligonucleotide (SEQ ID NO:62). In contrast, the singlet oligonucleotide showed no significant binding to nuclear proteins of similar mobility. The ATTG insertion/deletion (doublet/singlet) NFKB1 promoter polymorphism therefore is a determinant of nuclear protein binding to the promoter, probably a member of the NFkB gene family.

It is known that the NF-kB protein regulates the activity of the NFKB1 gene by interaction of NFkB gene with the NFKB1 promoter. The inventors have discovered that ATTG insertion/deletion promoter polymorphism is an important determinant of nuclear protein binding, and appears to specifically affect active NF-kB nuclear protein binding to the promoter. The ATTG insertion/deletion thus determines autoregulation of NF-kB protein of its own (NFKB1) gene transcription.

Individuals who carry only the NFKB1 singlet are not expected to have the same degree of nuclear protein-NFKB1 promoter interaction in comparison with individuals whose chromosomes have the ATTG doublet NFKB1 polymorphism. This has been amply supported by the data presented.

The −94ins/delATTG NKFB1 promoter polymorphism is a highly significant discovery, not only because it has been shown to be a determinant in developing ulcerative colitis, but also because it is likely to be involved in other NF-κB mediated complex genetic disorders. The inventors have demonstrated that this polymorphism has functional attributes, making it highly likely to be an important risk factor for immune mediated, complex genetic disorders as well as other diseases where the NFKB1 gene products, p50 or p105, play a role. Thus, NFKB1 associated functional genetic determinants may determine risk of their development as well.

A particular embodiment of the invention relates to a new method of identifying individuals at risk for one of the inflammatory diseases, inflammatory bowel disease and, in particular, the ulcerative colitis phenotype. This comprises first determining the presence of the particular alleles (genotype) of the ATTG ins/del polymorphism in the NKFB1 promoter. Individuals that carry the −94delATTG allele and especially individuals homozygous for this allele have a statistically greater risk of developing inflammatory bowel disease and, in particular, ulcerative colitis than individuals who do not have the −94ATTG ins/del polymorphism.

The invention provides a new methods for assessing risk or presence of disease, or dissecting disease pathophysiology by measuring binding of cellular nuclear proteins to nucleic acid segments isolated from the NFKB1 promoter. It is contemplated that as other polymorphisms of NFKB1 promoter are identified and associated with a disease manifestation, the NFKB1 polymorphisms may exhibit decreased binding to nuclear proteins compared with binding to wild type NFKB1 promoter that does not show this polymorphism. Increased risk of developing the disease or having an early stage of the disease could be determined by measuring differences in binding properties.

It is further contemplated that individuals having symptoms of inflammatory bowel disease can be treated with appropriate compositions that enhance binding of nuclear proteins to NKFB1 promoter. Such compositions can be formulated in pharmaceutically acceptable media suitable for human administration, preferably by oral administration. In cases of ulcerative colitis, the enhancers should be targeted to the colon where the effects of UC are manifest. Effective formulations and delivery vehicles of the appropriate compositions can be readily devised from well-known sources and available materials.

It is also contemplated that one can use gene therapy to identify a vector such as an attenuated virus that contains −94insATTG allelic sequences and will deliver a corrective NFKB1 gene or the corrective promoter sequence of the NFKB1 gene to cells in the targeted organ (such as the colon in persons with UC). Alternatively, stabilized olignonucleotides can be used to bind specifically to the NFKB1 promoter in-vivo to alter its activity in persons with NFK1 promoter genetically associated diseases, or persons at risk for such diseases. Such oligonucleotides can also be ligated to specific molecules that will alter NFKB1 promoter activity in order to specifically target these molecules to the ATTG polymorphic region and perhaps to activate binding at the 3' kappaB site or block binding by NFKB1-PIP. If an inhibitory element of NFKB1 is identified that binds a nuclear protein, inhibition of NFKB1 can be countered in persons with NFKB1 −94delATTG alleles by using antisense RNAs to bind to this element to block further down-regulation of NFKB1 promoter activity.

In another aspect of the invention, polynucleotide sequences are provided to allow for the preparation of relatively short DNA (or RNA) sequences that have the ability to specifically hybridize to the −94delATTG allele of the NFKB1 promoter. In such aspects, nucleic acid probes of an appropriate length are prepared based on a consideration of a selected NFKB1 gene sequence. The ability of such nucleic acid probes to specifically hybridize to the −94delATTG sequence allows use in a variety of assays for detecting the presence of complementary sequences in a given sample.

Preferred nucleic acid sequences employed for hybridization probes include sequences that are complementary to at least a 10 to 30 or so long nucleotide stretch of the −94 delATTG del/ins region of the NFKB1 promoter, as exemplified by the sequences shown as SEQ ID NO:2, SEQ ID NO:3, SEQ ID NO:4 and SEQ ID NO:5. A size of at least 10 nucleotides in length helps to ensure that the fragment will be of sufficient length to form a duplex molecule that is both stable and selective. Molecules having complementary sequences over stretches greater than 10 bases in length are generally preferred in order to increase stability and selectivity of the hybrid, and thereby improve the quality and degree of specific hybrid molecules. One generally prefers to design nucleic acid molecules having gene-complementary stretches of 15 to 20 nucleotides. Longer molecules may be prepared by chemical synthesis of the fragment.

One may desire to employ varying conditions of hybridization to achieve different degrees of selectivity of the probe toward the target sequence. To obtain a high degree of selectivity, relatively stringent conditions to form the hybrids should be used; for example, low salt and/or high temperature conditions such as provided by 0.02M-0.15M NaCl at temperatures of 50° C. to 70° C. These conditions are particularly selective and tolerate little, if any, mismatch between the probe and the target sequence.

In general, one may employ hybridization probes both as reagents in solution hybridization and in embodiments employing a solid phase. In embodiments involving a solid phase, the sample containing the target DNA (or RNA) is adsorbed or affixed to a selected matrix. The fixed single-stranded nucleic acid is then subjected to specific hybridization under desired conditions. The conditions depend, among others, on the criteria required, depending on the GC content, target region of the nucleic acid, and, importantly, the size of the probe. Following washing of the hybridized surface to remove nonspecifically bound probe molecules, specific hybridization is detected, or can be quantified, from the properties of the label, depending on the type of label employed.

Several effective probes are contemplated; however, each will be capable of detecting a −94delATTG or a −94insATTG polymorphism in a human NFKB1 promoter. A preferred probe will selectively bind at the −94deLATTG D allele of the kB promoter. The probe or probes selectively bind to kB promoter regions containing a singlet ATTG or ATTGATTG polymorphism or at least bind to that region with little interference from binding to regions that lack the polymorphism. Binding determination can be done by well-known methods, as discussed, generally under stringent hybridization conditions in order to preclude weak and nonspecific interaction.

The probes of the invention may more readily be detected by employing a detectable label, such as radioactive, enzymatic or other ligands such as avidin/biotin, which provide a detectable signal. In certain embodiments, an enzyme tag such as urease, alkaline phosphatase or peroxidase, instead of radioactive labels may be used. Antibody or fluorescent labels may also be conveniently employed. In preferred embodiments, a fluorescent label such as luciferase is employed.

In a related aspect, the present invention contemplates a diagnostic assay kit for detecting the presence of an −94delATTG polymorphism from a biological sample, particularly from humans. Such a kit will contain a specific −94delATTG allele probe of the present invention and may further contain reagents for detecting an interaction between the probe and the target gene allele. The probe is preferably labeled with a fluorescent tag, although other well-known detectable labels may be suitable. Exemplary probes designed to be highly specific for binding to the ATTG singlet ins/del polymorphic region are SEQ ID NO:4 and SEQ ID NO:5.

In a preferred embodiment the kit will include at least one probe specific for the ATTG singlet polymorphism and at least one probe that selectively binds the ATTG duplet. Each probe may be labeled with a different label so that the binding target can be distinguished.

Also within the scope of the invention are methods of treating individuals who exhibit symptoms of inflammatory bowel disease, such as ulcerative colitis. Treatments include administration of pharmaceutically acceptable compositions containing substances that will promote binding of cellular nuclear proteins and particularly NFKB1-PIP to the disclosed ATTG polymorphic −94del NFKB1 allele. Such methods will apply equally well to treating other diseases once the functional genetic component has been identified as it has with the ATTG polymorphism associated with UC.

BRIEF DESCRIPTION OF THE DRAWINGS

(FIG. 2B).

EMSAs using oligonucleotides that span the promoter polymorphic site reveal that strong binding to NP is observed with the complete wildtype sequence and weak or non-detectable binding with deletion or key mutation variants. NP derived from HeLa cells was incubated with the 22 bp wildtype oligonucleotide ('W', lane 1); or with 18 or 22 bp −94delATTG promoter polymorphism variants ('D', lane 2 or 'DL', lane 3, respectively); or with one of 3 mutant versions of the wildtype oligonucleotide ('Mut1, 2 or 3'). (FIG. 2C) NP expressed in colon but not ileal tissues binds to oligonucleotides of the wildtype NFKB1 promoter. EMSAs were performed using NP extracts made from endoscopic mucosal biopsies taken from normal colon and ileum. Equal amounts of NP were loaded onto an 8% non-denaturing gel (samples done in duplicates). NP from colon showed significantly greater binding to 'W' oligonucleotides than did NP from the ileum (compare lanes 1, 2 versus lanes 7, 8), whereas NP from colon and ileum showed similar binding to 'N' oligonucleotides, that contain the canonical NF-κB p50/p65 protein binding consensus sequence (lanes 11, 12 for colon and lanes 5, 6 for ileum) used as a control. 'D' oligonucleotides bind neither deal nor colonic NP (lanes 3, 4, 9 and 10).

FIG. 3 represents the −94del ATTG containing luciferase construct showing significantly less luciferase activity than the wild type construct.

FIG. 4A is an EMSA showing the binding of various nuclear extracts. HeLa cell nuclear extracts bind the duplet ATTG polymorphism. Nuclear proteins from HeLa cell nuclear extracts do not bind the singlet ATTG polymorphism. Nuclear proteins from HeLa cell nuclear extracts bind the extended singlet ATTG polymorphism to a lesser degree as compared to the duplet polymorphism. Other nuclear proteins from human cell nuclear extracts as well as from HeLa cell nuclear extracts bind equally to all three forms of the ATTG polymorphism.

DETAILED DESCRIPTION OF THE INVENTION

Figure 1:
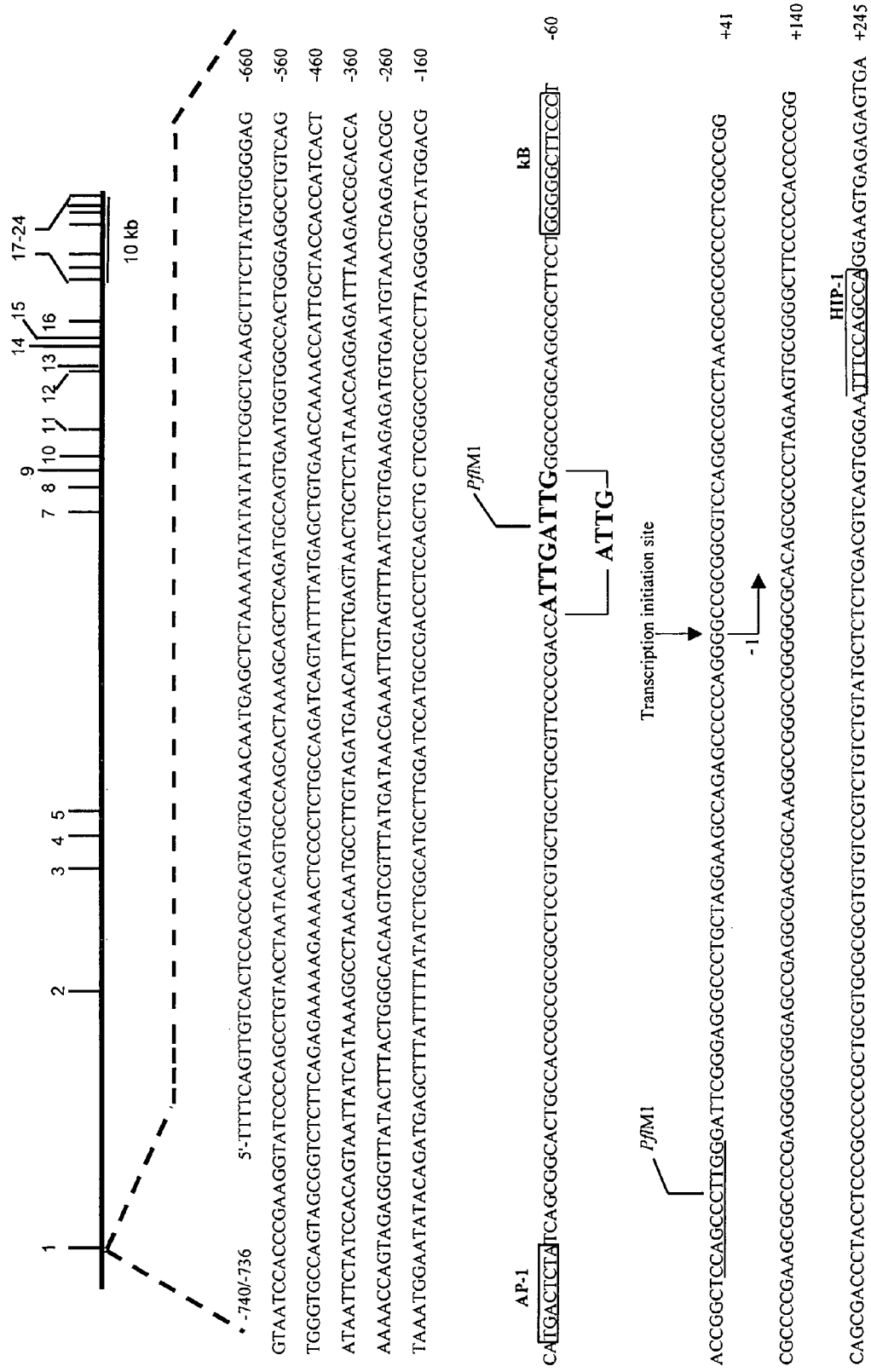
FIG. 1 shows the NFKB1 gene structure (SEQ ID NO: 1). The diagram for genomic structure with the location of the 24 exons (top) and sequence of the −740 by 5' of exon 1 through +245 (bottom) are shown. The transcription initiation site shown is the major site identified by Ten, et al. (1992). The −94 ins/del ATTG polymorphism is indicated in bold and large font. Pf(M) restrictions sites used for genotyping and AP-1, kB and HIP-1 DNA binding motifs are designated.

The invention is based on the discovery of a functional relationship between a NFKB1 gene promoter polymorphism and a human disease. The importance of the functional impact of a polymorphism in the NFKB1 promoter is the effect observed on the promoter activity. When NFKB1 protein binding to the NFKB1 gene promoter is inhibited, overexpression of NFKB1 affects several pathways involved in inflammatory response, particularly those related to cytokines. Identification of a NFKB1 promoter with identified functional polymorphisms now provides the capability to identify individuals at risk for a wide variety of pathological function, and to develop methods to restore normal promoter activity in those individuals harboring such promoter polymorphisms.

NFKB1 encodes the genes for the p50 and p105 NF-κB isoforms, ubiquitous transcription regulators important for multiple diseases and pathological states associated with inflammation and immunity, including inflammatory bowel disease (IBD). NFKB1 is a gene suspected to be involved in IBD, and particularly ulcerative colitis (UC), given the increased linkage evidence observed for the region of chromosome 4q24 containing NFKB1 in UC or mixed pedigrees, and given that an important mouse colitis model links to the region of mouse nfkb1. Six nucleotide variations detected from probands with increased linkage evidence to the region were further analyzed. A 4 bp promoter polymorphism, −94ins/delATTG, was chosen because it produced a relatively large sequence change and because its location proximal to binding sites important to promoter regulation.

Promoter-exon 1 constructs that contained the ATTG deletion (D) allele showed significantly reduced promoter activity in vitro. This was particularly pronounced following 24 h of exposure to LPS, a potent activator of NF-κB. Additionally, nuclear protein extracts from HT-29 human colonic epithelial cells and from HeLa cell lines, and extracts from mucosal biopsies from normal human colon tissues bound avidly and specifically to ATTG insertion (W) containing oligonucleotides. Conversely, nuclear proteins bound only weakly, or not at all, to ATTG deletion containing oligonucleotides (D).

The results suggested that the −94ins/delATTG polymorphism: (i) affects promoter activity of the NFKB1 gene, particularly following stimulation of the innate immune system by bacterial cell wall components (e.g. LPS); and (ii) contains nucleotides that, depending on the specific allele, differentially bind to an unidentified nuclear protein. Whether or not potential up-regulation of NFKB1 promoter activity by nuclear protein binding to the W and not the D allele accounts for the observed differences in NFKB1 in vitro promoter activity or whether the differences in activity is independent of this binding are not known. This may involve the identification of the nuclear protein that binds well to the W and not to the D oligonucleotides.

An important result of the cellular findings in the disclosed genetic studies was the −94ins/delATTG polymorphism evidenced from two independent functional assays, in vitro promoter activity and differential nuclear protein binding, indicating that the specific allele inherited has functional consequences. The −94ins/delATTG polymorphism thus represents the first demonstration of a functional NFKB1 polymorphism. Its association with diseases (like UC, believed to be mediated by NF-κB) is therefore significant because its presence can be used to identify individuals not only exhibiting symptoms of these diseases but also to determine those at risk for the disease.

Interestingly, the major locus, cdcs1, for the severe colitis phenotype of C3H/HeJBir-IL10 knockout mice is located where the mouse (nfkb1) homolog to human NFKB1 maps, and thus nfkb1 has been previously proposed as a candidate gene for this mouse model and NFKB1 as a candidate gene for human colitis. In a 1998 North American genome-wide screen in multiplex IBD pedigrees, there was evidence for linkage present on chromosome 4q24 where NFKB1 maps (multipoint non-parametric logarithm of the odds, MLod=1.71, P=2.5×10$^{-3}$). Evidence for linkage in this region was greater for the 'mixed' families (containing at least one UC and one CD patient); the uncorrected MLod was 2.76 (P=1.9×10$^{-4}$). A British/German (Hampe, Schreiber, et al., 1999) and a Canadian (Rioux, Silverberg, et al., 2000) IBD genome-wide screens both found evidence to support linkage in the same overall region, in UC sibling pairs and 'all IBD' pedigrees, respectively.

The −94ins/delATTG polymorphic alleles initially were tested for association with UC, CD and IBD in 235 pedigrees containing one or more affected offspring. Using several different analytic schemes, the D allele was observed to be in LD with the UC phenotype. However, the association was of borderline significance, perhaps because of the limited sample size given the modest transmission to non-transmission ratio. These findings were strengthened by comparing the allele and genotype frequencies in probands with those of controls. There was stronger evidence of D allele association with UC using this method. The TDT results are consistent with the case-control results, indicating that the observed case-control association is unlikely to be secondary to population stratification between cases and controls because the TDT use of within family controls precludes this potential problem.

The case-control association required separation of non-Jewish and Jewish Caucasian cases and controls because it was observed that allele frequencies were different for controls based on ethnicity. The non-Jewish results were significant, yet the Jewish results were not, perhaps secondary to small sample size and/or a weaker genetic effect. Nonetheless, the trend of greater D alleles in UC cases as compared to controls was similar for both the Jewish and non-Jewish populations studied. It is more expected for a potential functional polymorphic allele that associations will be present for diseases independent of ethnicity. This finding is not always observed, even for established associations; for example, the functionally demonstrated 702Trp NOD2 allele (also less common in Jewish than non-Jewish Caucasian patients) has been observed to be even less common in Jewish CD patients than controls. However, any significance of the NFKB1 promoter polymorphism in the Jewish population remains uncertain, although trends may be detected in a larger set of subjects.

The −94delATTG-UC association was replicated using an independent, second set of non-Jewish UC cases and healthy controls. The overall odds ratio (calculated from both sets of samples) of the DD homozygote genotype was modest (odds ratio 1.59). The modest genotypic risk observed fits with models of inheritance proposed for complex genetic disorders; multiple low penetrant risk alleles of different genes have been hypothesized to account for overall genetic risk (41). The weak linkage evidence found in the family samples is not surprising (and may be even greater than expected) given the low odds ratio of the risk genotype. There can be other polymorphisms on other genes in the region and even within non-coding regions of NFKB1 that may be functional and contribute even greater risk to developing UC, yet this does not invalidate the present observations that −94delATTG is associated and has a functional effect.

The heterozygote (WD) genotype was not associated with IBD risk. This indicates that a single W allele abrogates risk from (and may be dominant over) the UC associated D allele.

In vitro promoter expression studies indicated that the D allele may result in relatively decreased NFKB1 message and hence decreased p50/p105 NF-κB protein production. This was unexpected because it was in contrast to initial expectations in view of the association of UC with increased levels of NF-κB. Parallel findings have been observed for the CD associated NOD2 mutations: in vitro studies in NOD2 transfected cell lines show that NOD2 mutations result in a decrease rather than an expected increase in NF-κB activity (Bonen, Ogura, et al., 2003).

Recently, mutant NOD2 was shown to be defective in clearing invasive bacteria in comparison to wild type NOD2 (Hisamatsu, Suzuki, et al., 2003). Thus, one hypothesis is that poor activation of NF-κB may weaken the normal cellular defenses against intestinal bacteria by the innate immune system. This defect may allow bacteria that cross the intestinal lumen to not be properly cleared by the immune system, and hence contribute to on-going intestinal inflammation characteristic of CD.

Thus decreased NFKB1 D allele gene expression appears to cause a decrease in NF-kB p50/p65 heterodimers, major mediators of inflammation, in turn affecting the ability of the colon to be protected from colonic bacteria. Support for this concept is the finding that p50 deficient mice have greater susceptibility to infection from some (*Listeria monocytogenes* and *Streptococcus pneumoniae*) but not all (*Haemophilus influenza* and *Escherichia coli*) types of bacteria (Sha, Liou, et al., 1995).

Alternatively, reduced NFKB1 gene expression may result in increased risk of UC because p50, unlike p65, does not contain a transactivation domain and can in some cases inhibit inflammation. p50 homodimers (also products of NFKB1) may be involved in blocking p65 dimers from binding to promoters and activating genes involved in inflammatory cascades (Erdman, Fox, et al., 2001). In mouse macrophage cell lines, p50 over-expression was shown to inhibit tumor necrosis factor-α (TNF-α) gene expression, and the mechanism of p50 inhibition appears to depend on NF-κB binding sites that have preferential affinity for p50 homodimers. Overexpression of p50 homodimers has also been suggested as the mechanism of LPS refractoriness following repetitive stimulation of mononuclear phagocytes. Nonetheless, p50 may have dual roles as p50-deficient mice are refractory to the induction of arthritis models, and p50 alone can stimulate C-reactive protein expression, although this induction is considerably less than p50/p65 heterodimer stimulation.

Additional polymorphisms or mutations in the promoter, exon 1 and exon 2 regions evaluated were not found to account for the observed D association with UC. This was examined by sequencing these same regions using DNA from an additional 12 unrelated patients all with DD genotypes. No additional polymorphisms were observed. Hence, including the seven D chromosomes reported in Table 1, only the −94ins/delATTG and exon 1+252C>G polymorphisms in 31 D containing chromosomes were found. Additionally, these two polymorphisms are in near complete LD. The two most common haplotypes (−94insATTG-exon 1+252C and −94delATTG-exon 1+252G) were observed in 72 out of 74 total chromosomes genotyped. Therefore, either polymorphism will yield essentially equivalent information for testing potential NFKB1 promoter/exon-1 associations. Genetically, it is unlikely that the D association with UC can be easily separated from the expected corresponding exon 1+252G association with UC if the exon 1+252C>G polymorphism also has an effect on gene expression.

Extending the present promoter/exon-1 luciferase construct studies to include the exon 1+252 polymorphism region and test constructs that contain the D and W alleles with either the C or G exon 1+252 alleles will determine if this polymorphism has a similar effect. It is unlikely that there exist common, functionally relevant, NFKB1 coding polymorphisms in exons 3 through 24. Although only a modest number of chromosomes were screened in this study, Wintermeyer et al. (Wintermeyer, Riess, et al, 2002) screened 96 Parkinson's disease patients and Miterski et al. (Miterski, Bohringer, et al., 2002) screened a large number (exact figures not reported) of multiple sclerosis patients and healthy controls (apparently 100 controls given the Leu614Phe frequency noted below) for NFKB1 coding polymorphisms/mutations. Both studies used very high sensitivity methods of single-strand conformation polymorphism analysis (SSCP) and reported success in completely screening all exons, except for exons 1 and 2. The two studies observed the relatively common exon 12+77C>T silent polymorphism, a rare exon 8 silent polymorphism in one Parkinson's disease patient and a Leu614Phe exon 17 mutation in 0.5% of controls in the multiple sclerosis study.

The −94ins/delATTG promoter polymorphic site has functional consequences. Electrophoretic mobility shift assays show that oligonucleotides containing the wildtype (−94insATTG) sequence and not those containing the deletion (−94delATTG) bind to a nuclear protein, NFKB1-promoter interactive protein (NFKB1-PIP). Moreover, wildtype −94insATTG binds to nuclear proteins isolated from colonic epithelian cell lines and normal human colonic tissue, but not ileal tissue. This complements findings that the −94ins/delATTG association is associated with UC and not CD because UC involves the colon whereas CD most often involves the ileum.

When NFKB1 promoter/luciferase reporter constructs designed to assay transcriptional activation were transfected into HeLa and HT29 cells, differential expression was observed between the −94insATTG and −94delATTG constructs following lipopolysaccharide (LPS) stimulation. NFKB1 promoter activity is auto-regulated by NF-kB proteins via the Kb binding site. Located only 19 bp 3' of the −94ins/delATTG polymorphism. The marked differential activity following LPS stimulation as well as the proximity of the kB binding site strongly suggests an interaction between the −94insATTG polymorphism binding and the kB regulatory site. This interaction may be altered for the −94delATTG polymorphism and likely involves the NFLB1-PIP nuclear binding that is characteristic of the −94insATTG polymorphism. The inventors believe that loss of this binding plays an important role in the genetic association of −94delATTG with UC.

EXAMPLES

Materials and Methods
Subjects for the TDT and Case-Control Studies

Informed consent for participation in molecular genetic studies was obtained from all study subjects and ethical approval was given from each center's institutional review boards. In addition, DNA samples from two CEPH controls (133101, 133102) were obtained from Coriell Institute for Medical Research (NIGMS Human Genetic Mutant Cell Repository Camden, N.J.).

For TDT studies, DNA samples from all available parent/child pedigrees with a UC offspring and a similar number of pedigrees with a CD offspring were used. These pedigrees were from an extended set of an IBD family collection, ascertained by the IBD Genetic Studies of Johns Hopkins University, University of Chicago and University of Pittsburgh, described previously (Ogura, Bonen, et al., 2001). Briefly, DNA was purified from blood samples obtained from North American, non-Hispanic Caucasian families with one or more cases of IBD, diagnosed as UC, CD or indeterminate colitis. The case notes of all patients were reviewed and diagnoses were confirmed by standard endoscopic, histopathological, and radiological criteria. Subjects were classified as Ashkenazi Jewish. UC, CD or IBD probands from these pedigrees were also compared with controls ascertained by Johns Hopkins University and University of Chicago.

For the case-control replication, we genotyped DNA samples from a separate set of non-Jewish, non-Hispanic, Caucasian UC patients, that were not members of families genotyped for the TDT studies and for whom DNA samples on parents were unavailable. Additional DNA samples were genotyped from non-Jewish, non-Hispanic, Caucasian UC patients recruited from the University of Toronto IBD center. The 'set B' non-Jewish, non-Hispanic control DNA samples genotyped were from healthy individuals, randomly ascertained from a population based cohort study, the NYCP for longitudinal follow up for future development of cancer. The NYCP has enrolled approximately 20 000 normal subjects from the New York Metropolitan area between the ages of 35 and 60 since 1999. In addition to blood samples, data on ethnicity of the subject, their parents and grandparents, as well as a general medical history and a family history of cancer is obtained during a face-to-face interview of each subject.

Sequencing NFKB1 for Detection of Polymorphisms

To detect NFKB1 sequence variations, DNA samples were initially sequenced from 12 subjects (all Caucasian, three Jewish) to give 95% power to detect polymorphisms with a frequency of >5% (Kruglyak, et al., 2001). Using NFKB1 specific primers (Table 1), designed on the basis of the published NFKB1 genomic DNA sequences (accession AF213884, gi 7012904), PCR was used to amplify overlapping fragments of the promoter and exon 1 (from position −889 5' of a NFKB1 major transcription initiation site) and all 23 coding exons as well as >25 bp of each coding exon's flanking intron sequence. PCR was performed, in a 50 µl reaction mixture containing 15 ng of genomic DNA, under the following conditions: denaturation at 95° C. for 30 s, annealing at 56° C. and extension at 72° C. for 1 min, amplification for 35 cycles. The annealing temperature for amplifying GC rich and promoter regions was 60° C. Amplified DNA fragments were purified by spin column centrifugation through a selective adsorption silica-gel matrix (QIAquick PCR Purification Kit Qiagen Cat. No. 28104) and then sequenced on an ABI 3700 fluorescent capillary sequencer. Sequences of amplified fragments were compared with each other and with the published NFKB1 genomic DNA sequence to identify variants. Additional UC DD homozygotes were sequenced to identify more rare variants for the promoter, exon 1 and exon 2 region that may be in LD with the D allele.

TABLE 1

PRIMERS USED FOR SEQUENCING NFKB1 and EXPRESSION CONSTRUCTS

| Primer Name | Forward primer 5' to 3' | Reverse primer 5' to 3' |
| --- | --- | --- |
| Promoter b | tccagaaaaacactccacca SEQ ID NO: 6 | accttcgggtggattacctc SEQ ID NO: 7 |
| Promoter c | ttcagttgtcactccaccca SEQ ID NO: 8 | ggtggtagcaatggttttgg SEQ ID NO: 9 |
| Promoter d | aaagaaaactcccctctgcc SEQ ID NO: 10 | ttccatttaagcgtgtctcag SEQ ID NO: 11 |
| Promoter e | tttaatctgtgaagagatgtgaatg SEQ ID NO: 12 | gtagggaagcccccagga SEQ ID NO: 13 |
| Promoter f | gcccttaggggctatgga SEQ ID NO: 14 | ctctggcttcctagcaggg SEQ ID NO: 15 |
| Promoter g | gttccccgaccattgattg SEQ ID NO: 16 | aagcccgcacttctaggg SEQ ID NO: 17 |
| Pro c-F + h-R | ttcagttgtcactccaccca SEQ ID NO: 18 | ctctctcacttcctggctgg SEQ ID NO: 19 |
| Exon 2 | gcgagcttaacacgagggta SEQ ID NO: 20 | gtgtgaaagcgggtgtaagtt SEQ ID NO: 21 |
| Exon 3 | acgtaaacgttgtccaaccc SEQ ID NO: 22 | aaaccatacaaggggtaattgaga SEQ ID NO: 23 |
| Exon 4 | tgccatcacctttcaacaaa SEQ ID NO: 24 | tgaggctcaggacagtgtga SEQ ID NO: 25 |
| Exon 5 | tacggagccctctttcacag SEQ ID NO: 26 | gaaggcaacccgtactcatt SEQ ID NO: 27 |
| Exon 6 | tgtttccatgttgctggaga SEQ ID NO: 28 | gagggtctcagaaaggtccc SEQ ID NO: 29 |
| Exon 7 | aatgcatgtagccccaagag SEQ ID NO: 30 | gatgaaaaccaaagcctgga SEQ ID NO: 31 |
| Exon 8 | ttgggctttataaaagcatgg SEQ ID NO: 32 | ctggacatcaacctttcaagc SEQ ID NO: 33 |

TABLE 1-continued

PRIMERS USED FOR SEQUENCING NFKB1 and EXPRESSION CONSTRUCTS

| Primer Name | Forward primer 5' to 3' | Reverse primer 5' to 3' |
|---|---|---|
| Exon 9 | ttggtcatgtgtgctaaggg SEQ ID NO: 34 | gcagcagagggatgtttctt SEQ ID NO: 35 |
| Exon 10 | Gactgaaccttttgatcttgttttt SEQ ID NO: 36 | Gagacaggaggatccctcaa SEQ ID NO: 37 |
| Exon 11 | ctccaggacacggtgttttt SEQ ID NO: 38 | ctgtttgaggccaggagttc SEQ ID NO: 39 |
| Exon 12 | aacgcttcttgaaatttaccatc SEQ ID NO: 40 | tcatagccactcaactcacaga SEQ ID NO: 41 |
| Exon 13 | gtcctgtcacaccaaaggct SEQ ID NO: 42 | tgcattcatcaattatttgtcaaga SEQ ID NO: 43 |
| Exon 14 | ttttcttttcctttttgcagc SEQ ID NO: 44 | tgcttttccaaaggcataca SEQ ID NO: 45 |
| Exon 15 | tccttaagcatgccataccc SEQ ID NO: 46 | ttccaacagatgacagcagc SEQ ID NO: 47 |
| Exon 16 | ttcaaaacattttagggccaa SEQ ID NO: 48 | caaaggtttgttttgttttgc SEQ ID NO: 49 |
| Exon 17 | cagtatggccccacctattg SEQ ID NO: 50 | agcactttgggtgcaaatc SEQ ID NO: 51 |
| Exons 18-19 | tttactgtccctccccatga SEQ ID NO: 52 | aagttgggtttgcattcctg SEQ ID NO: 53 |
| Exon 20 | atccaggagattgcctcaag SEQ ID NO: 54 | aaaggcatgttctttgggg SEQ ID NO: 55 |
| Exons 21-22 | acattagggtaccaggccc SEQ ID NO: 56 | aacggggaaaatctgaaggt SEQ ID NO: 57 |
| Exon 23 | agccgaaacaggaaacttga SEQ ID NO: 58 | ccaggggtagagagacaca SEQ ID NO: 59 |
| Exon 24 | catgagcttttagagcccg SEQ ID NO: 60 | tgctgtggtcagaaggaatg SEQ ID NO: 61 |

Genotyping the −94delATTG Promoter Polymorphism

A restriction enzyme digestion assay was used to genotype the −94ins/delATTG polymorphism for Johns Hopkins, University of Chicago and New York Cancer Project samples. A 289 bp PCR fragment was amplified from genomic DNA using the 'promoter e' forward and 'promoter f' reverse primers (Table 1, SEQ ID NO:12, SEQ ID:13, SEQ ID NO:14, SEQ ID NO:15). Products were digested by the enzyme PflM1, which cleaves the −94insATTG containing product twice and the −94delATTG containing product once (FIG. 1), and analyzed on a 2.5% agarose gel.

University of Pittsburgh samples were genotyped for the polymorphism using the same primers but with the forward primer end labeled with fluorescent dye, and the presence or absence of the 4 bp deletion was determined by the size of the labeled PCR product on an ABI 3700 sequencer.

The University of Toronto samples were genotyped using the ABI Prism SNapShot kit. A 190 bp fragment of DNA, encompassing the site of the −94delATTG polymorphism, was first amplified by PCR. The PCR product was purified of unincorporated dNTPs as well as single stranded DNA/primers using shrimp alkaline phosphatase and exonuclease I, respectively. The purified fragment was then used as the template for the SNapShot reaction. Primers that were complimentary to the wild type −94insATTG sequence and deletion −94delATTG sequence were designed in the 5' forward and 3' reverse directions SEQ ID NO:6-SEQ ID NO:61) and differentially labeled by a fluorophore. Each primer ended at the nucleotide immediately preceding the 5'-most ' A-nucleotide' of the PflMI restriction enzyme cleavage site (FIG. 1). A single base pair extension revealed each allele discriminated by size and differential fluorophore emissions detected by 3100 and 3700 ABI sequencers and data was analyzed with GeneScan and/or GeneMapper software.

Twelve DNA samples, four for each of the three possible genotypes (homozygote wildtype, heterozygote and homozygote deletion) whose sequences were determined by direct sequencing, were used as blinded controls for all three genotyping methods.

Statistical Analysis

Transmission disequilibrium tests. The presence of LD between the NFKB1 promoter polymorphism and UC, CD and IBD was determined using the family-based association tests in Genehunter 2.1, FBAT (Family Based Association Test) and the PDT (Pedigree Disequilibrium Test).

The TDT analysis implemented in Genehunter 2.1 performs the traditional TDT (Spielman, McGinnis, et al., 1993) using all genotyped parent child trios in the families. In this analysis, transmissions from homozygous parents are not counted (they provide a transmitted and an untransmitted copy of the same allele) and cases where one parent is missing are used only when the genotyped parent and the proband are both distinct heterozygotes. The cases where both parents and the proband have the same heterozygous genotypes are counted (as a transmission and non-transmission of each allele).

Programs FBAT and PDT were used to test for LD independent of linkage. Both FBAT and PDT allow for inclusion of triads, discordant sibships as well as extended families and will incorporate data from multiple affected sibships in the analysis while adjusting for their non-independence. The FBAT also uses data from nuclear families, sibships or a combination of the two, to test for association between traits and genotypes. If data are available on pedigrees, the program decomposes each pedigree into individual nuclear families or sibships. The program constructs, by default, a test of the null hypothesis: no linkage and no association; testing for both, linkage in the presence of LD. Using option '-e', it computes the test statistic using the empirical variance, as described by Lake et al. (Lake, Blacker, et al., 2000). This option should be used when testing for association in an area of known linkage and data from multiple sibs in a family are used. Distortion of transmission from parents to offspring is assessed by an observed/expected chi-square test.

The PDT summarizes the results in two global scores the 'sumPDT', summarizing the level of significance from all families, and the 'avePDT', weighting the contribution of larger families to ensure that their contribution to the end result does not exceed that of the smaller families.

Case-control analyses. Comparison of allele frequencies and genotypes between cases and controls was done using Fisher's exact test of proportions. For individuals from multiply affected IBD pedigrees, only one individual from each pedigree, specifically, the first individual with UC, CD or IBD enrolled from their family into the study, was used for the respective analyses.

Electrophoretic Mobility-Shift Assays (EMSAs)

Figure 2A:
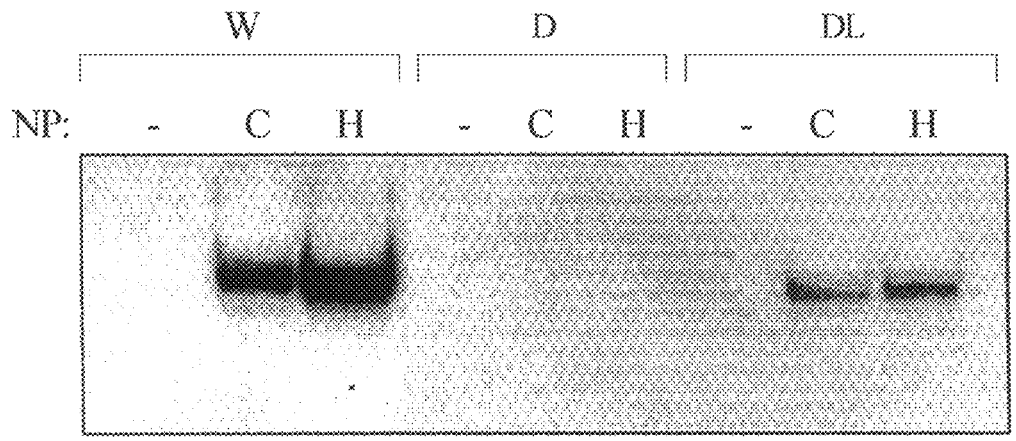
FIGS. 2A-C show Electrophoretic Mobility Shift Assays (EMSAs). The wildtype oligonucleotides (but not deletion oligonucleotides) show specific binding to human colonic tissues and epithelial culture cells. (A). The EMSA show differential binding of nuclear proteins (NP) derived from two human epithelial colonic cell lines, CaCo2 cells ('C') or HT-29 cells ('H'), to oligonucleotides of wildtype ('W') or deletion variants ('D' and 'DL'). Sequence identities are given in (FIG. 2B) (SEQ ID NOS 74, 75, 79 and 76-78, respectively, in order of appearance). $^{32}$P-labeled double-stranded oligonucleotides were incubated with buffer ('dash'), or with NP extracts.
Figure 2B:
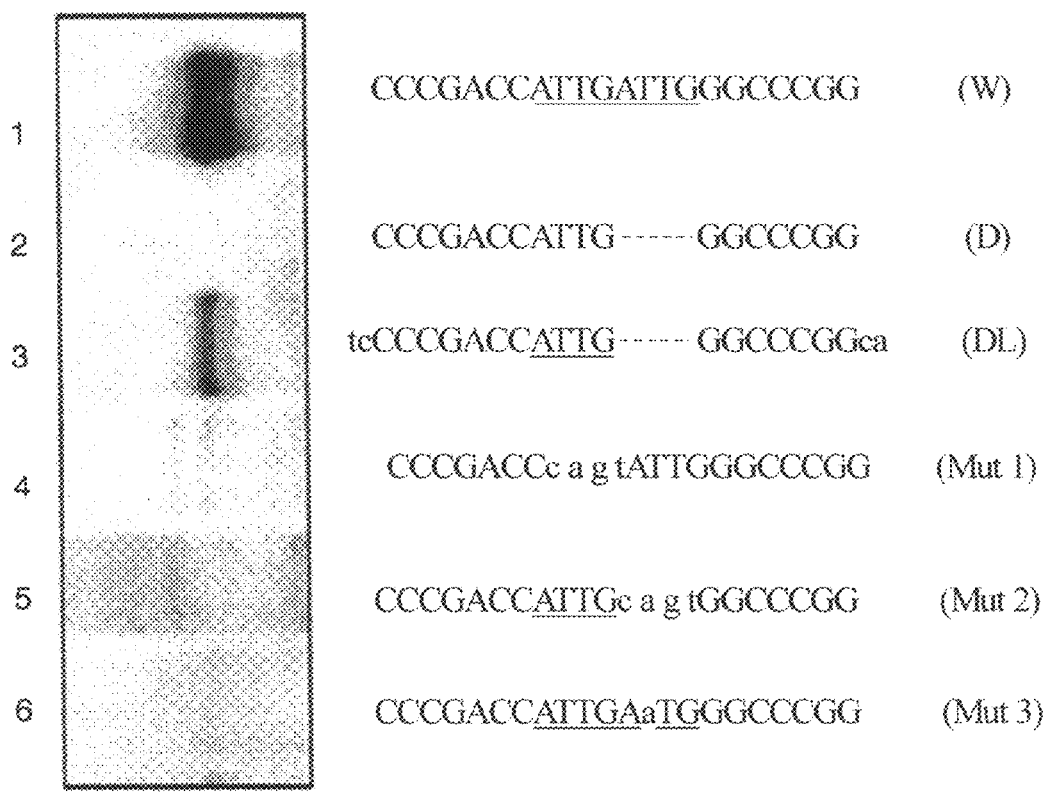

Nuclear protein extracts were made from 90% confluent human tissue-culture cells grown at 37° C. with 5% $CO_2$ in DMEM supplemented with 10% fetal bovine serum (FBS) and streptomycin/ampicillin, or were extracted from colonic and ileal biopsies of normal mucosa from two individuals without IBD nor other inflammatory disorders or diarrheal diseases, that had undergone colonoscopy screening for colonic polyps. Biopsies were obtained following informed consent. Each of the nuclear protein extracts was made using the NE-PER kit from Pierce (Milwaukee, Mich., Cat. #78833) as per manufacturer's instructions. Complimentary single-stranded oligonucleotide probes were synthesized based on the NFKB1 promoter ('W', 'D' and 'DL'; FIG. 2B) or the canonical NF-κB p50/p65 protein binding consensus sequence, 5'-AGTTGAGGGGACTTTCCCAGGC-3'; (SEQ ID NO:62) was used as a control for equal protein loading. An additional 4-base overhang (gatc) was added at the 5' ends of each oligonucleotide to optimize end-labeling with $^{32}P$. Complimentary oligomers were allowed to anneal, and then radioactively labeled with dATP [$\alpha$-$^{32}P$] and dCTP [$\alpha$-$^{32}P$]. Following purification by Qiagen the labeled, double-stranded DNA oligomers were then incubated for 30 min with individual nuclear extract samples at room temperature. Electrophoretic Mobility Shift Assays (EMSAs) were performed as previously described.

Plasmid Construction of Luciferase Reporter Genes

The promoter-exon 1 region of the NFKB1 containing genomic sequence from nucleotides −736 to +245 (FIG. 1) was prepared by PCR amplification of either −94insATTG homozygote or −94delATTG homozygote human genomic DNA using primers Pro c-F and Pro h-R (Table 1; SEQ ID NO:18 AND SEQ ID NO:19). The PCR products were purified by agarose gel electrophoresis, extracted from gel slices (QIAprep miniprep kit; Qiagen Inc., Chatsworth, Calif.), and cloned into the pCR II-TOPO vector (Invitrogen, San Diego, Calif.). After restriction digestion with KpnI and XhoI, the NF-κB promoter fragment was cloned directionally into the pGL3-Basic firefly luciferase expression vector (Promega, Madison, Wis.) between unique KpnI and XhoI sites. Restriction analysis and complete DNA sequencing confirmed the orientation and integrity of each construct's inserts.

Transient Transfection/Reporter Assay

HeLa human cervical adenocarcinoma and HT 29 human epithelial colon cancer cell lines were obtained from American Type Culture Collection (Rockville, Md.). Cells were grown in Dulbecco's modified Eagle's (DME)/high glucose medium supplemented with 10% fetal bovine serum, 1 mm sodium pyruvate, 100 U/ml of penicillin G and 100 μg/ml streptomycin (Life Technologies, Inc.) at 37° C. in 5% $CO_2$. Subconfluent cells cultured in 24 well dishes were transiently co-transfected with 0.4 μg of either pGL3-W or pGL3-D reporter vector (FIG. 3) and 5 ng of the thymidine kinase promoter-*Renilla* luciferase control vector (phRL-TK, Promega) using 0.611 of FuGENE6 as per manufacturer's specifications (Roche Molecular Biochemicals, Indianapolis, Ind.). The phRL-TK vector contains the herpes simplex virus thymidine kinase promoter and was co-transfected as an internal control for transfection efficiency (Grentzmann, Ingram, et al., 1998). The concentrations of each PGL3-W and PGL3-D vectors were determined, following Qiagen purification procedure in parallel, by an average of 10 spectrophotometric readings.

Transfection using pGL3-Basic vector without an insert was used as a negative control. Twenty-four hours after transfection, the cells were cultured in 10% serum medium or with exposure to 1 μg/ml of *E. coli* derived lipopolysaccharides (LPS: Serotype 055:5B) for 6-24 h. Cells were then lysed, and firefly and *Renilla* luciferase activities were measured simultaneously in each sample using the Dual-Luciferase Reporter Assay System according to the manufacturer's instructions (Promega). Firefly luciferase activities were normalized to *Renilla* luciferase activity as 'relative luciferase activity'. The data presented are means of six independent experiments. The results are expressed as the mean plus standard error of the mean. Statistical analyses were performed using Stat View software for Macintosh version 5.0 (SAS Institute Inc.). Unpaired Student's t-tests were used for comparisons. A P-value of 0.05 was considered to be statistically significant.

EXAMPLES

Example 1

Polymorphism Detection in the NFKB1 Gene

The NFKB1 promoter, exon 1 and all 23 coding exons and their flanking introns (FIG. 1, top) were sequenced using DNA from 12 unrelated subjects: two Centre d'Etude du Polymorphisme Humain (CEPH) controls and 10 probands from pedigrees with the greatest evidence for linkage, as noted by maximal family non-parametric linkage (NPL) scores, to the NFKB1 region in a 1998 IBD genome screen. Six nucleotide variations were detected (Table 2). Five were novel: an insertion/deletion polymorphism of four bases in the 5' promoter region (−94ins/delATTG) (FIG. 1, bottom), an exon 1 polymorphism located within the 5' untranslated region of NFKB1 message and three intronic variants. A previously described exon 12+77C>T silent polymorphism was also observed.

TABLE 2

FKB1 nucleotide variations detected

| Nucleotide charge | CEPH 133101 | CEPH 133102 | No. of rare/total alleles sequenced |
|---|---|---|---|
| Promoter −94ins/delATTG | ins/ins | ins/del | 7/24 |
| Exon 1 + 252C > G | C/C | C/G | 7/24 |
| Exon 12 + 77C > T | T/C | C/C | 2/24 |
| IVS15 − 25G > T | T/G | G|G | 3/24 |
| IVS22 + 15C > T | C/C | C/T | 1/24 |
| IVS22 + 22C > G | C/G | C/C | 5/24 |

Genetic Association of the NFKB1 Promoter −94delATTG Allele with UC

Of the six variations detected, only the −94ins/delATTG appeared to have a potential functional role. It involved the deletion of multiple nucleotides and is located between two putative key promoter regulatory elements (FIG. 1), the most proximal was a functional KB binding site located 19 base pairs 3'. The −94ins/delATTG polymorphism in 235 singleton and multiplex IBD pedigrees was analyzed for association with UC, CD or IBD phenotype.

Promoter and exon 1 numbering is based on the major transcription initiation site of Ten et al. (1992) and reference sequence AF213884. Alternatively, exon 1+252C>G and exon 12+77C>T may be described as 5 UTR −449C>G and C1143T based on the open reading frame noted.

TDT analysis using the program Genehunter 2.1 showed 100 transmissions to 71 non-transmissions of the −94delATTG (D) allele to UC offspring (P=0.027, Table 2). There was also increased transmission of the D allele in all IBD pedigrees (206 to 170) although this trend did not reach the 0.05 level of significance. There was no evidence for association with the CD phenotype. The results of non-parametric linkage analysis using Genehunter 2.1 on the 126 families (96 informative) that contained either one or more siblings or other non-parent child IBD affected relative pairs showed slight evidence of linkage for the IBD phenotype (NPL 1.7; P=0.04).

Two additional TDT programs were used, Family Based Association Test (FBAT) (35) and the Pedigree Disequilibrium Test (PDT). Both packages provide valid tests of LD independent of linkage using different analytic schemes. Using the different analytic outcomes provided, both tests showed borderline significant LD evidence for the association of the D allele with the UC phenotype, independent of linkage (FBAT, P=0.052; PDT, global score sum P=0.047) (Table 2). The PDT also showed significant evidence for IBD (P=0.035, Table 3).

TABLE 3

TDT association analyses showing families with offspring with corresponding affection status

| Affection status | UC | CD | IBD |
|---|---|---|---|
| No. of families[a] | 131 | 122 | 235 |
| No. of affecteds[b] | 187 | 220 | 433 |
| Total no. of trios | 161 | 199 | 366 |
| Simple trio pedigrees | 105 | 57 | 122 |
| Sibling pair pedigrees[c] | 23 | 59 | 103 |
| Extended pedigrees[d] | 3 | 6 | 10 |
| Genehunter 2.1 | | | |
| Transmitted allele D | 100 | 137 | 206 |
| Non-transmitted allele D | 71 | 126 | 170 |
| $x^2$ | 4.92 | 0.46 | 3.45 |
| P-value | 0.027 | 0.50 | 0.06 |
| FBAT | | | |
| P-value | 0.028 | 0.96 | 0.06 |
| P-value −e | 0.052 | 0.96 | 0.09 |
| PDT | | | |
| Global score sum PDT | | | |
| $x^2$ | 3.948 | 0.168 | 2.036 |
| P-value | 0.047 | 0.682 | 0.154 |
| Global score ave PDT | | | |
| $x^2$ | 3.424 | 1.08 | 4.45 |
| P-value | 0.064 | 0.299 | 0.035 |

[a]24 IBD families had both UC and CD offspring and the UC and CD offspring were also analyzed separately with the other pedigrees having only UC and CD offspring, respectively. Six families had only offspring with indeterminate colitis and were included only in the 'IBD' analyses and not the UC or CD analyses.
[b]Number of affecteds listed for UC offspring families include only pedigree members with UC and vice-versa for number of affecteds listed for CD offspring families.
[c]Includes two UC and seven CD pedigrees with three affected siblings, and one CD and one mixed pedigree with four affected siblings.
[d]'Extended pedigree', pedigrees containing more than one affected offspring with either one or more affected cousin pairs, affected avuncular pairs or three generations of affected individuals with DNA samples on grandparents, parents and affected child.
Numbers in bold denote P-values ≦ 0.05.

Case-Control Analysis and Replication of the −94delATTG Association with UC

Based on these TDT results, the study was extended to compare the frequency of the D allele and DD genotype in cases and controls. Such case-control studies are frequently more powerful measures of allelic association (depending on allele frequencies) than comparable TDT analyses. These analyses were also performed to determine the specific genotypes [homozygote insertion or wildtype (WW), heterozygote (WD) or homozygote deletion (DD)] that resulted in increased risk of the D allele in our UC and IBD pedigrees. The D allele was more frequent in non-Jewish, unrelated UC or IBD probands (from the same IBD pedigrees examined in the TDT analyses) than among ethnically matched controls (P=0.015 and 0.014, respectively; Table 4, set A). These UC and IBD probands were also significantly more frequent carriers of the DD genotype (P=0.040 and 0.041, respectively) than controls. The D allele showed a trend towards increased frequency in Jewish UC patients versus controls (43.6 to 34.2%), although this did not reach statistical significance (P=0.088). For both non-Jewish and Jewish ethnicities, the relative increase in D allele frequencies and DD genotypes in patients as compared to controls was greater for the subset of UC patients than all IBD patients.

For a replication study, 141 new, unrelated non-Jewish UC patients from the IBD Genetic Studies of Johns Hopkins, University of Chicago and University of Pittsburgh were genotyped, along with an independent set of 117 unrelated, non-Jewish UC patients from a recently characterized University of Toronto cohort. D allele frequencies for the second set of Hopkins/Chicago/Pittsburgh UC samples (f=0.440) and the University of Toronto UC samples (f=0.449) were similar. For controls, 653 non-Jewish Caucasians obtained from a population based cohort study, the New York Cancer Project (NYCP), were genotyped. For the total replicate sample set (set B), the D allele and DD genotype frequencies for UC patients were significantly greater than the respective control frequencies (0.444 versus 0.391, P=0.021 and 0.205 versus 0.150, P=0.029, respectively) (Table 4). Combining all unrelated non-Jewish Caucasian UC samples (from sets A and B) and combining all non-Jewish Caucasian controls shows that the homozygous DD genotype provides a significant-yet moderate-risk for developing UC [0.214 versus 0.148, odds ratio 1.57 (95% confidence interval 1.14-2.16); P=0.004]. The heterozygote (WD) genotype frequencies were similar for all UC cases and controls (0.477 versus 0.479).

TABLE 4

Case-control analyses

| Set | Phenotype | No. | WW | WD | DD | D allele frequency | P-value,[a] D allele frequency | P-value,[a] DD versus DW or WW |
|---|---|---|---|---|---|---|---|---|
| A | Controls-NJ | 149 | 0.389 | 0.470 | 0.141 | 0.376 | | |
|   | UC-NJ | 92 | 0.283 | 0.478 | 0.239 | 0.478 | 0.015 | 0.040 |
|   | CD-NJ | 74 | 0.311 | 0.527 | 0.162 | 0.426 | 0.170 | 0.410 |
|   | IBD-NJ | 156 | 0.295 | 0.481 | 0.224 | 0.465 | 0.014 | 0.041 |
|   | Controls-J | 142 | 0.430 | 0.458 | 0.113 | 0.342 | | |
|   | UC-J | 39 | 0.308 | 0.513 | 0.179 | 0.436 | 0.088 | 0.182 |
|   | CD-J | 48 | 0.417 | 0.438 | 0.146 | 0.365 | 0.385 | 0.352 |
|   | IBD-J | 79 | 0.354 | 0.506 | 0.139 | 0.392 | 0.167 | 0.353 |
| B | Controls-NJ | 653 | 0.369 | 0.481 | 0.150 | 0.391 | | |
|   | UC-NJ | 258 | 0.318 | 0.477 | 0.205 | 0.444 | 0.0212 | 0.0285 |
| A + B | Controls-NJ | 802 | 0.372 | 0.479 | 0.148 | 0.388 | | |
|   | UC-NJ | 350 | 0.309 | 0.477 | 0.214 | 0.453 | 0.0020 | 0.0043 |

NJ, non-Jewish; J, Ashkenazi Jewish.
[a]P-values are for comparisons between UC, CD or IBD cases and ethnically matched controls for each set.
Numbers in bold denote P-values ≦ 0.05.

Example 2

−94ins/delATTG Polymorphism Nuclear Protein Binding to NFKB1 Promoter

Electrophoretic Mobility Shift Assays (EMSA) were performed to assess if the −94ins/delATTG polymorphism is within a binding domain for nuclear proteins. Oligonucleotides that contained the wildtype sequence ('W') showed strong binding to nuclear protein extracted from two human colonic epithelial cell lines, CaCo2 and HT-29 (FIG. 2A). In contrast, the deletion oligonucleotide ('D') showed no binding. The 'DL' oligonucleotide (containing only a single ATTG deletion allele but with four additional NFKB1 nucleotides added 5' and 3' to make a deletion oligonucleotide with the same length as 'W') appeared to allow minimal binding of proteins of similar mobility. This binding was markedly less than that of the 'W' oligonucleotide.

To assess the specificity of the observed DNA-protein interaction, mutations were made of the tandem ATTG residues at the polymorphic site. Mutating the most 5' ATTG to CAGT (FIG. 2B, lane 4) resulted in a near complete loss of binding to HeLa-cell derived nuclear protein (as compared to the 'W' oligonucleotide, lane 1), whereas mutating the second (i.e. 3') ATTG to CAGT resulted in no detectable binding (lane 5). Furthermore, mutating the first 'T' of the second ATTG at this site reduced binding to negligible levels (lane 6).

Figure 2C:
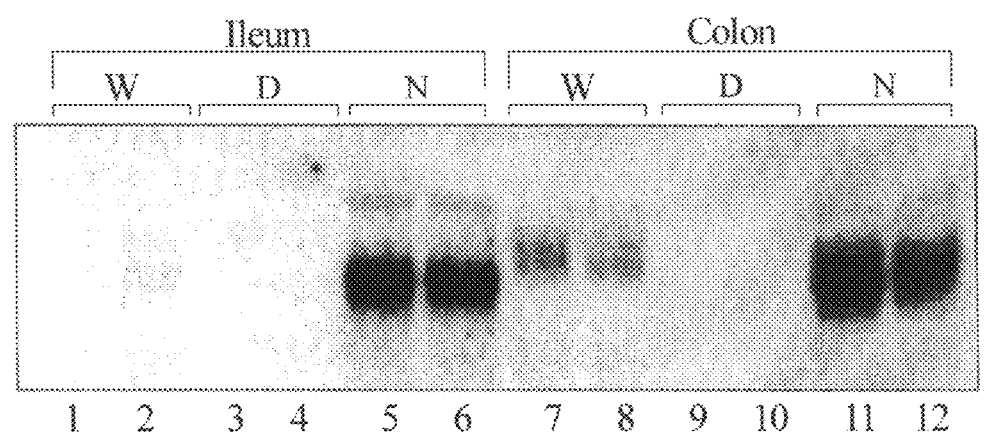

Nuclear protein binding observed using cell culture extracts and human intestinal tissue extracts was investigated. Consistent with the results from colonic cell lines, nuclear proteins extracted from normal human colonic mucosa bound to 'W' but not 'D' oligonucleotides (FIG. 2C, lanes 7-10). Alternatively, there was no specific evidence that nuclear proteins of the same mobility from normal terminal ileal mucosa bound to the 'W' nor 'D' oligonucleotides (lanes 1-4). The presence of the binding protein in colonic rather than ileal tissues is intriguing because of showing that NFKB1 is genetically associated with UC, a disease where inflammation only involves the colon, but is not associated with CD, a disease where inflammation is frequently found limited to the ileum without colonic involvement.

Example 3

Figure 3A:
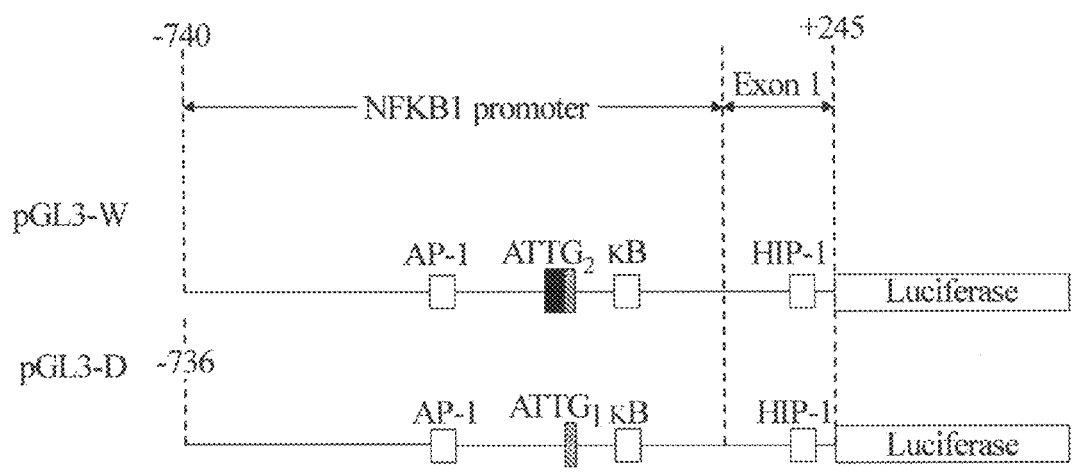
FIG. 3A is pGL3-W wild type promoter construct (top) and pGL3-D, −94delATTG construct (bottom), which were transiently transfected into HeLa and HT29 cells.
Figure 3B:
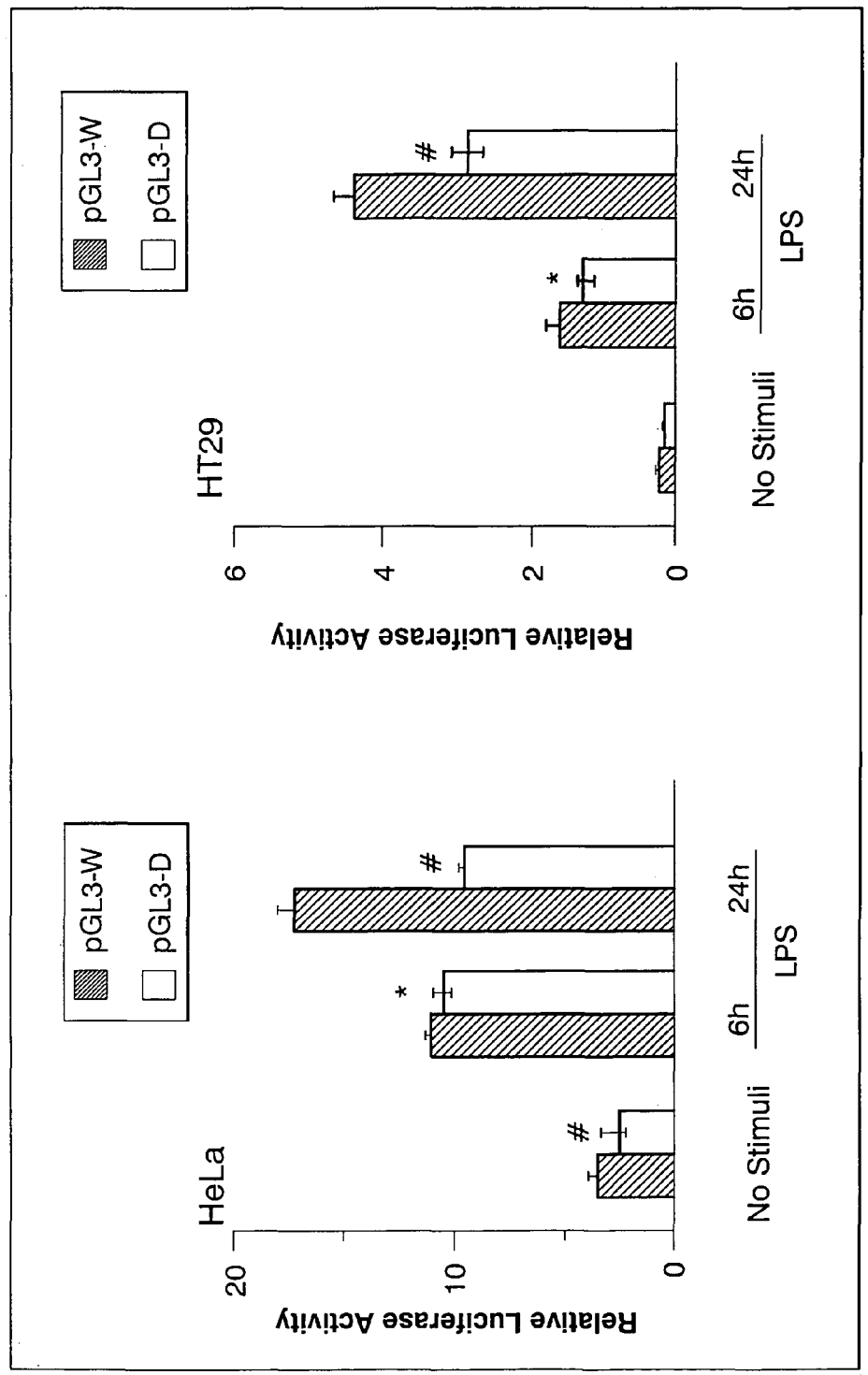
FIG. 3B shows relative luciferase activity for the NFKB1 pGLW (solid bars) and pGL3-D (open bars) promoter (exon 1 constructs are shown at baseline, and 6 hr and 24 hr following stimulation with lipopolysaccharide (LPS, *E. coli* 055:B5 1 µg/ml). #P<=0.0005; *P<0.05.

NFKB1 Promoter-Luciferase Reporter Constructs Show Decreased Promoter Activity for the Deletion Polymorphism in Transient Transfection Experiments HeLa and HT 29 cells were transiently transfected with either pGL3-W or pGL3-D reporter constructs (FIG. 3A). These constructs contained 736 bp of the 3' region of the NFKB1 promoter with the W allele ($ATTG_2$) or 732 bp of the same region with the D allele ($ATTG_1$). Each construct also included the most 5' 245 bp of exon 1 (i.e. the same sequences as shown in FIG. 1). The regions cloned into both constructs include the Activator Protein-1 (AP-1) and κB nuclear protein binding consensus sequences in the promoter, and the putative HIP-1, Housekeeping Initiator Protein I, motif in exon 1. These transcriptional regulatory elements of NFKB1 have been previously identified and shown to be important for NFKB1 gene promoter activity (Ten et al., (1992); Cogswell et al., 1993). The constructs did not include the exon 1+252C>G polymorphism sequence. The thymidine kinase (TK) promoter-*Renilla* luciferase plasmid (phRL-TK) was co-transfected to control for differences in transfection efficiency.

pGL3-D transfected HeLa cells showed significantly reduced relative luciferase activity at baseline (pGL3-W, 3.28±0.08 versus pGL3-D, 2.52±0.26, P=0.005; FIG. 3B). Incubation for 6 h with 1 μg/ml lipopolysaccharide extract (LPS), a potent activator of both NF-κB and NFKB1 transcription, markedly increased relative luciferase activity by more than 3-fold from baseline for both pGL3-W and pGL3-D transfected HeLa cells. Yet LPS stimulated pGL3-D activity remained significantly lower than stimulated pGL3-W activity (FIG. 3B). At 24 h of LPS exposure, pGL3-W but not pGL3-D transfected HeLa cells showed a further increase in relative luciferase activity from that observed at 6 h. In fact, pGL3-W induced relative luciferase activity was 82% greater than pGL3-D relative luciferase activity at 24 h of LPS exposure (pGL3-W, 17.46±0.34 versus pGL3-D, 9.57±0.16, P<0.0001).

For HT-29 colonic epithelial cells, baseline relative luciferase activity for both constructs was very low (<5% of HeLa cells). There was a slight, but non-significant decrease in the pGL3-D transfected versus pGL3-W transfected cells. Similar to that observed for the HeLa cells, transfected HT-29 pGL3-W activity was significantly higher than pGL3-D activity following 6 h of LPS stimulation. Higher pGL3-W relative luciferase activity was most pronounced following 24 h of LPS stimulation (pGL3-W, 4.42±0.21 versus pGL3-D, 2.85±0.15, P=0.0001). Transfected pGL3-basic vector plasmid alone showed <0.01% of the relative luciferase activity as compared to the PGL3-W or PGL3-D constructs at baseline and after LPS stimulation for both cell types.

Example 4

Nuclear Protein Binding to ATTG Polymorphic Oligonucleotides

Oligonucleotides (FIG. 1) containing either an ATTG singlet or ATTG duplet sequence and 6 bp of the NFKB1 promoter sequence immediately 5' and 3' of this position, and 5' overhand sequences were constructed by standard DNA oligo synthesis. A second oligonucleotide having the complementary NFKB1 sequence and 5' over hand sequence was developed for each ATTG polymorphic oligonucleotide. These oligonucleotides were allowed to anneal to form double stranded oligonucleotides, were end labeled with $P^{32}$ and then hybridized with nuclear proteins extracted from mammalian or human cells or tissues. A double stranded oligonucleotide containing an established NFKappa B binding consensus sequence was similarly constructed but not labeled.

Cells were purified from tissues and from cells in culture from rat liver, human HELA cells, Caco2 cells, HT29 cells, and human colon biopsies using Ficoll density gradient centrifugation. Nuclear proteins were purified from the purified cells or tissues using the method of Standke et al. (1994) and Waxman et al. (1995).

Electromobility shift assays (EMSA's) were performed as follows: Double-stranded oligonucleotides were prepared by combining and heating equimolar amounts of the complementary single-stranded DNA to 95° C. for 10 min in a solution containing 50 mM Tris-HCl, pH 7.5, and 100 mM NaCl followed by cooling to room temperature over 3 h. The annealed oligonucleotides were diluted to a concentration of 2 μM and stored at −20° C. EMSA were carried out in 25 μl containing 25 mM HEPES, pH 7.8, 50 mM KCl, 0.1 mM EDTA, 1 mM dithiothreitol, 10% glycerol, and 2 μg of poly (dI.dC) (Pharmacia LKB Biotechnology Inc.). End-labeled DNA (0.1-0.5 ng) were incubated with various amounts of nuclear extracts for 20 min at room temperature after which 5 μl of 0.2% bromphenol blue/xylene cyanol were added, and samples were loaded on a 4 or 5% nondenaturing polyacrylamide gel (acrylamide:bisacrylamide=39:1) in low ionic strength. For competition experiments, nuclear extracts were first incubated with unlabeled oliognucleotides in molar excess for 5 min at room temperature prior to the addition of labeled DNA. For the "supershift" experiment, 1 μl of rabbit antiserum directed against NFKB p65, P50, AP2, and USF or non-immune serum was added to the reaction mixture at the end of the binding reaction, and an additional 30 min of incubation was carried out before loading samples onto the gel.

Protein extract was electrophoresed on polyacrylamide gels. Shift and "supershift" of labeled oligonucleotide was observed by autoradiography. The position of gel migration of autoradiography bands that denoted the labeled oligonucleotide mobility was compared from either (1) labeled oligonucleotide that had been mixed with nuclear protein extract alone or (2) with protein extract and antibody both in comparison to (3) the position of bands of the labeled oligonucleotide alone (without protein extract or antibody).

Figure 4:
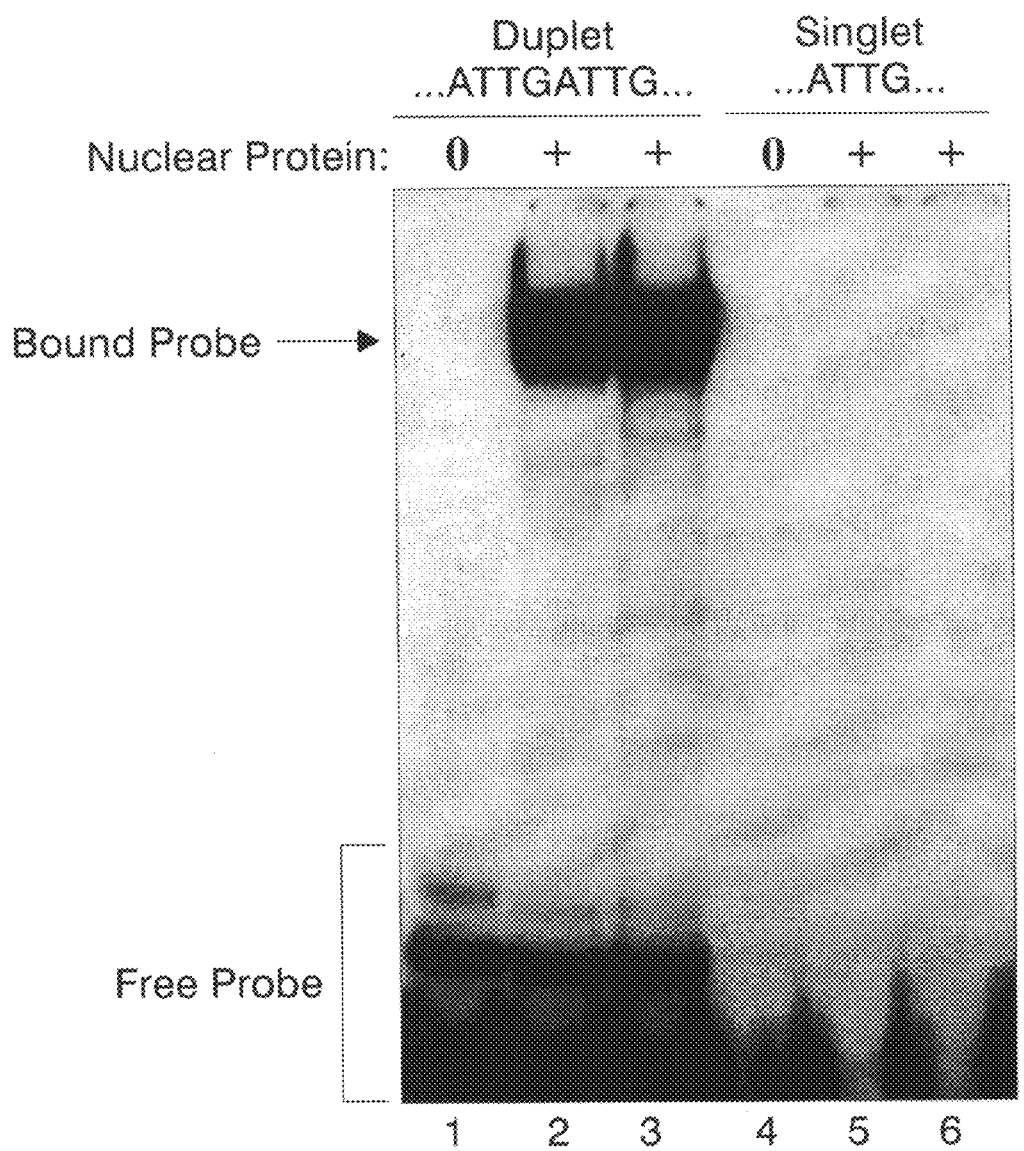
FIG. 4 is an electromobility shift assay (EMSA) showing binding properties of rat nuclear proteins to NF-kB1 promoter ATTG deletion/insertion polymorphism. Nuclear proteins isolated from rat liver extracts bind the NF-kB1 promoter polymorphism duplet ATTG, but do not bind the NF-kB1 promoter polymorphism singlet ATTG. Nuclear proteins isolated from rat liver extracts exhibit decreased binding to the extended form of the singlet ATTG polymorphism of the NF-kB1 promoter (extended by two nucleotides on each of the 5' and 3' ends).

Rat liver nuclear protein extract showed binding to the duplet oligo A in the form of two bands that showed markedly decreased migration and thus relative high molecular weight (FIG. 4). No shift was seen with extract incubated with oligo B and minimal binding occurred with incubation with oligo C as denoted by similarly sized but relatively faint bands in comparison to those seen with oligo A. The two bands that bound to oligo A were competed with in a dose dependent manner by the NFKappa B unlabeled consensus sequence. FIG. 4A also shows that Hela cell protein extract had proteins of similar size (as the rat liver proteins) that caused by migration of oligo A to be slowed and was also competed with by oligo D. This extract showed virtually no binding to oligo B and minimal binding to oligo C.

Figure 5:
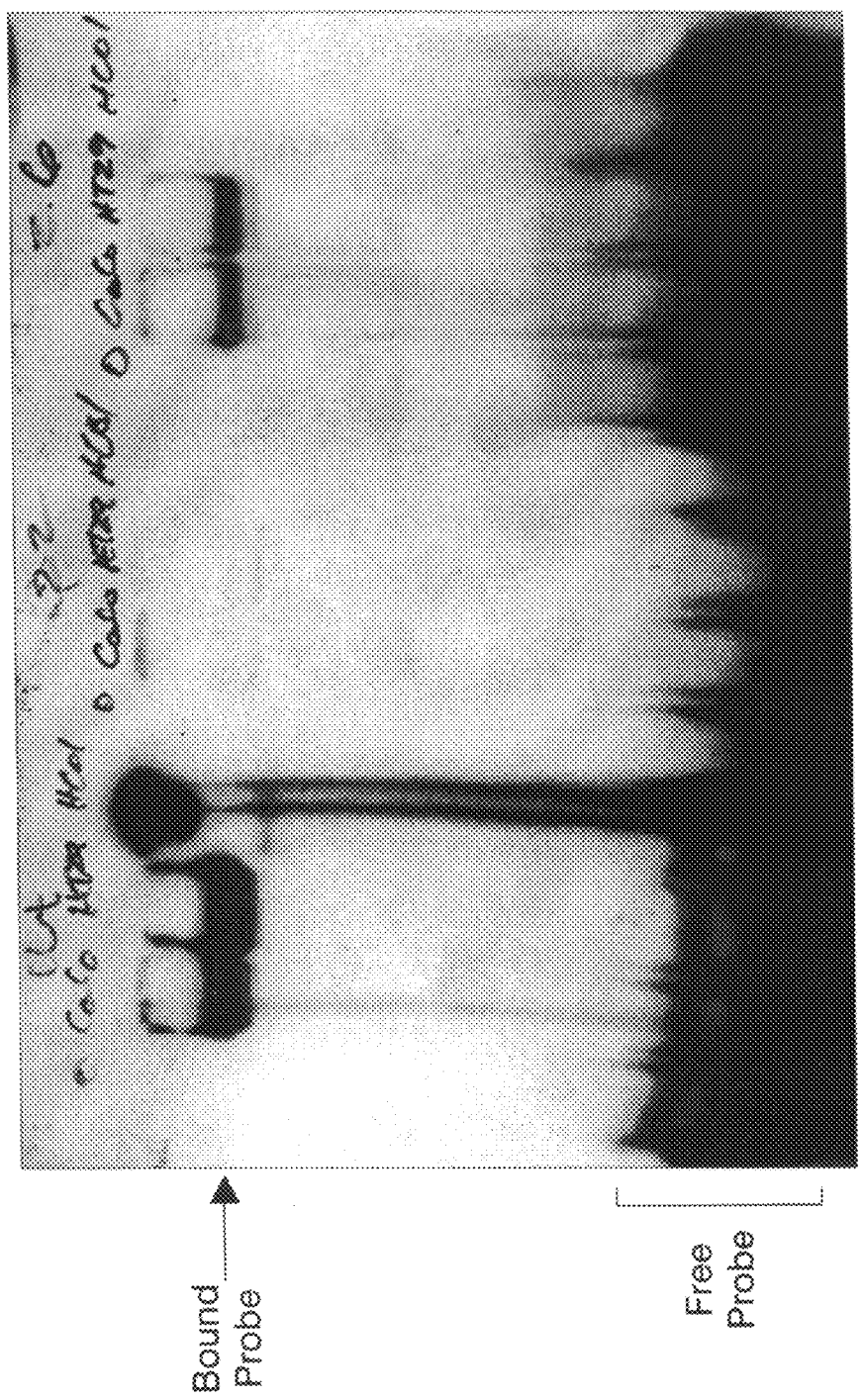
FIG. 5 shows oligonucleotide probe binding to CaCo2, HT29 and human colonic tissue.
Figure 6:
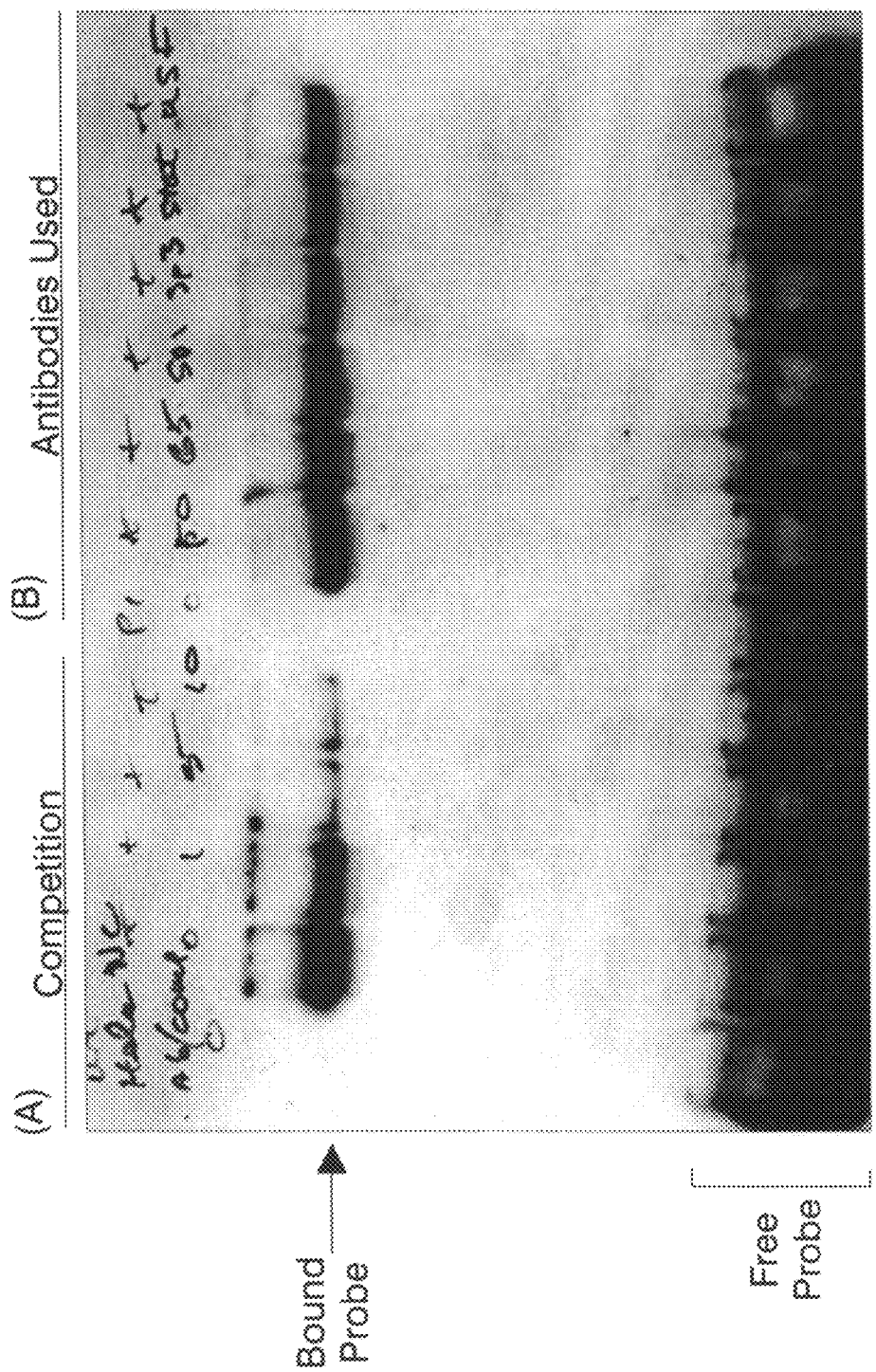
FIG. 6 shows competition experiments using antibodies to p50, p65, SP1, SP3, STAT and USF indicating that the bound probe might be blocking antibody to protein. Identification of the bound proteins employed EMSA
Figure 7:
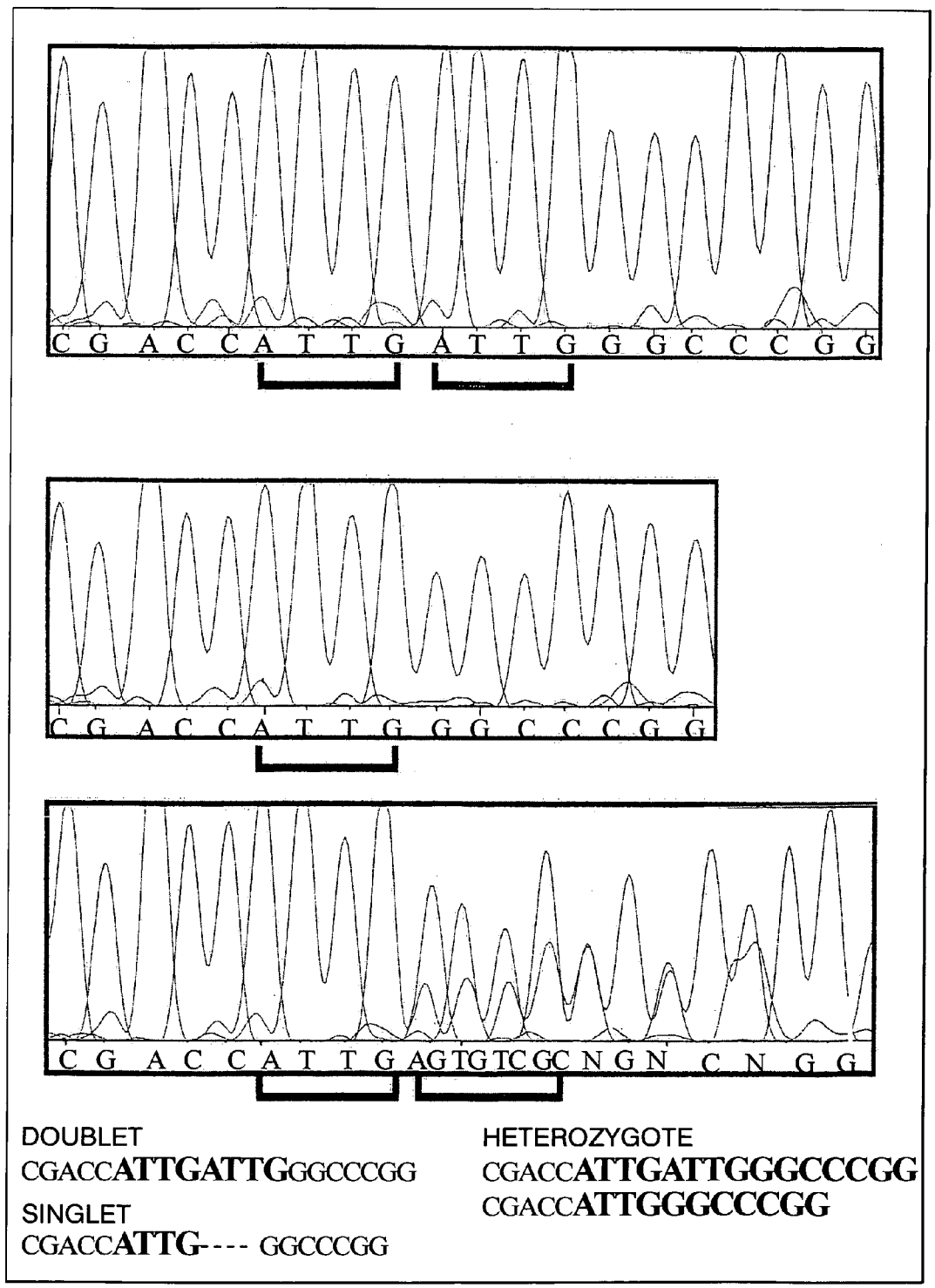
FIG. 7 shows fluorescent DNA sequence tracings of the doublet and singlet ATTG and a tracing obtained from a heterozygote (SEQ ID NOS 80-87, respectively, in order of appearance).

FIG. 5 shows oligonucleotide binding to CaCo2, HT29 and human colonic tissue. SUPERSHIFT experiments with antibodies to p50, p65, SP1, SP3, STAT and USF did not exhibit a mobility change (FIG. 6), indicating that in this experiment the oligomer might be blocking the binding of antibody to protein or that protein bound to the labeled oligomer is possibly a novel promoter binding protein.

Oligonucleotides that contain the NFKB1 ATTG singlet polymorphism show markedly decreased to absent binding of rat and human nuclear proteins in comparison to oligonucleotides that contain the NFKB1 duplet ATTG polymorphism. Competition studies suggest that at least some of the proteins that differentially bind to the ATTG polymorphic region are proteins (or subunits) of the NFKappaB family or proteins with similar nuclear binding properties.

Example 5

Identification of NFKB1-PIP

The novel NFKB1-PIP protein will be isolated and characterized as follows. The same NFKB1 −94insATTG double stranded oligonucleotide probe (W) found to bind in EMSA tests will be biotinylated at the 5' end with 15-atom spacer (Biotin-TEG; Qiagen] and hybridized to nuclear protein purified from HeLa cells. The probe/NFKB1-PIP complex will be magnetically separated from the nuclear protein pool using streptavidin-conjugated magnetic microbeads. Following enzymatic digestion, the molecular weight of NFKB1-PIP peptide fragments will be determined by matrix-assisted laser desorption/ionization-time of flight mass spectrometry (MALDI-TOF MS) available at the Johns Hopkins Digestive Disease Center Proteomics Core Facility. Concurrently, the same purification assay, but using the −94delATTG probe, will be performed as a negative control. An in-silico screen (TBLASTN) of the public databases using the peptide sequence as probes will be used to identify the cDNA. If the NFKB1-PIP matching cDNAs are novel or incomplete, the full coding region of NFKB1-PIP will be obtained by RT-PCR amplification and 5' & 3' rapid amplification of cDNA ends (RACE) using human colon RNA and NFKB1-PIP-specific oligonucleotide primers. If there is no match for NFKB1-PIP, nucleotide probes from the sequenced NFKB1-PIP peptides will be developed to screen human colon cDNA libraries. Additionally, a search of transcription factors databases yielded 6 potential binding elements to the −94insATTG. These factors can be evaluated as possible candidates using various immunochemistry and molecular biology techniques.

Example 6

NFKB1-PIP Expression and Localization

NFKB1-PIP/GFP (green fluorescent protein) fusion expression vector will be constructed and transfected into an appropriate cell line. To confirm that the expressed NFKB1-PIP clone is the correct protein, EMSAs will be performed using the "W" probe to analyze the gel's fluorescence pattern. Confocal microscopy will be used to determine if NFKB1 PIP/GFP protein is localized in the nucleus before and after LPS stimulation in lymphocyte, HeLa and HT29 cells. The NFKB1-PIP tissue distribution will be determined by using cDNA fragments identified in Example 5 to probe commercially available multiple tissue Northern Blot Panels (Clontech). Expression profiles will be quantified using real-time PCR in individual cell components of the colon; notably, epithelial cells, lymphocytes, macrophages, monocytes and fibroblasts isolated from resected human colon tissue. Real-time PCR will be used to determine if there are differences in expression levels of NFKB1-PIP in colon and small intestine biopsy tissues from a collection of 60 samples from IBD patients and normal controls in the John Hopkins University repository (Baltimore, Md.).

Example 7

Regulation of NKFB1 Expression by NFKB1-PIP

NFKB1-PIP levels will be reduced in HT29 and HeLa cells by introducing NFKB1-PIP short interfering RNA (siRNA). Using previously developed NFKB1 promoter luciferase reporter constructs (Karban & Okazaki, 2004), the effect of this reduction on the baseline and LPS-stimulated activities of the NFKB1 wildtype promoter will be assessed.

A transcription binding database has been searched and several transcription factors that are know to have consensus binding sequences in common with NFKB1 –94insATTG (duplet) allele region but not (or markedly less binding) to the –94delATTG (singlet) allele region (Tables 5-7).

NFKB1-PIP isolated using the described method will be tested for homology to these transcription factors. Alternatively, supershift assays (similar to that as shown for the experiments in FIG. 5) using antibody to any of these known transcription factors can be used to confirm NFKB1-PIP. Immunoprecipitation with such antibodies of NFKB1-pIP hybridized to "W" oligonucleotide may also be employed.

TABLE 5

JASPER TRANSCRIPTION FACTORS

| factor | Sequence | From | To | Score | Strand |
|---|---|---|---|---|---|
| c-MYB_1 | gaccattg SEQ ID NO: 63 | 4 | 11 | 7.065 | + |
| Yin-Yang | accatt SEQ ID NO: 64 | 5 | 10 | 7.027 | + |
| SOX-9 | ccattgatt SEQ ID NO: 65 | 6 | 14 | 10.640 | – |
| ATHB5 | cattgattg SEQ ID NO: 66 | 7 | 15 | 9.967 | + |
| Gfi | cattgattgg SEQ ID NO: 67 | 7 | 16 | 10.236 | – |
| Athb-1 | attgattg SEQ ID NO: 68 | 8 | 15 | 7.554 | – |
| Sox-5 | attgatt SEQ ID NO: 69 | 8 | 14 | 6.624 | – |
| Nkx | ttgattg SEQ ID NO: 70 | 9 | 15 | 5.189 | + |
| GATA-1 | tgattg SEQ ID NO: 71 | 10 | 15 | 5.403 | + |

TABLE 5-continued

JASPER TRANSCRIPTION FACTORS

| factor | Sequence | From | To | Score | Strand |
|---|---|---|---|---|---|
| GATA-2 | tgatt SEQ ID NO: 72 | 10 | 14 | 4.000 | + |
| GATA-3 | tgattg SEQ ID NO: 73 | 10 | 15 | 7.127 | + |

Sequence view tgattg: GATA-3
    tgatt: GATA-2 [+]
    tgattg: GATA-1 [+]
   ttgattg: Nkx [+]
  attgatt: Sox-5 [–]
  attgattg: Athb-1 [–]
 cattgattgg: Gfi [–]
 cattgattg: ATHB5 [+]
ccattgatt: SOX-9 [–]
    accatt: Yin-Yang [+]
   gaccattg: c-MYB 1 [+]

attg2 cccgaccattgattgggcccgg (SEQ ID NO: 74)
           |          |
          10      20

The methods, techniques and compositions disclosed and claimed herein can be made and executed without undue experimentation in light of the present disclosure. While the compositions and methods of this invention have been illustrated with several examples and preferred embodiments, it will be apparent to those of skill in the art that variations may be applied to the methods and compositions, in the steps or in the sequence of steps and in modifications of the compositions without departing from the concept, spirit and scope of the invention. Accordingly, the exclusive rights sought to be patented are as described in the claims below.

Example 8

Double stranded oligonucleotides that contain the ATTG doublet and the NFKB1 nucleotides immediately 5' of the doublet and the NFKB1 nucleotides immediately 3' of the doublet bind to a nuclear protein of humans and rats (termed NFKB1-promoter interactive protein or "NFKB1-PIP"). It is likely that other species contain homologous isoforms of this NFKB1-PIP. NFKIB1-PIP will interact with the NFKB1 promoter DNA in humans that have the –94insATTG allele to a greater degree than humans that have the –94delATTG allele. The inventors have developed a method to identify NFKB1-PIP by using double stranded oligonucleotides that contain the ATTG duplet and surrounding NFKB1 sequences. Examples of suitable oligonucleotides include: oligonucleotide "W", 5'-CCCGACCATTGATTGGGCCCGG-3' (SEQ. ID NO:74). This "W" oligonucleotide can be used (with or without minor modifications such as creating a four base nucleotide overhand extension of 5'-GATC-3') to "trap" the NFKB1-PIP. Attaching the "W" oligonucleotide to a magnetic bead, to a resin in a column or to a heavy molecule such as a polymer can be used to bind and then isolate NFKB1-PIP.

In contrast, because NFKB1-PIP binds poorly or not at all to identical olignonucleotides to "W" but with either a single ATG or a mutation in the 3' ATG (e.g. AATG), these ATTG singlet or mutated ATTG-doublet olignonucleotides can be used in a similar fashion to bind proteins that are not NFKB1-PIP but also bid the "W" oligonucleotide. Because these latter oligonucleotides do not bind the NFKB1-PIP well, these latter oligonucleotides can be used to remove non-specific proteins that are not NFKB1-PIP or to compare the sequence of proteins that bind these latter olignoucleotides with the proteins that bind the "W" olignoucleotide or similar olignucleotides, all in an effort to identify NFKIB1-PIP.

Isolating NFKB1-PIP will identify an important nuclear protein that has consequences of regulating nuclear protein activity such as NFKB1. NFKB1-PIP is likely also to be involved in regulating inflammation, acute stress reactions and apoptosis. It may provide protection of person with the −94insATTG allele from diseases like UC. NFKB1-PIP may be involved with either protection or pathophysiology of other diseases that involve NFKB1 and will likely have effects on other genes, either directly on their promoter or other sequences or indirectly through important pathways.

Control of NFKB1 promoter activity may be attained by identifying chemicals or RNA or DNA molecules that enhance or interfere with NFKB1-PIP binding to NFKB1 promoter in persons with the −94insATTG allele. The identified olignonucleotide sequences that bind strongly to NFKB1-PIP or oligonucleotides or with comparable effects may be used to identify those molecules that alter the NFKB1-PIP interaction with NFKB1 promoter. Similarly, the olignoucleotide molecules that bind poorly or not at all to NFKB1-PIP but are identical except for a single ATTG (e.g., oligonucleotide "D") or a mutant of the ATTG duplet can be used to identify molecules that allow NFKB1-PIP to bind to the NFKB1 delATTG promoter.

Furthermore, the disclosed constructs (see FIG. 2A and methods below) that contain allele specific NFKB1 promoter sequence (either the ATG duplet or singlet) with the downstream (3') reporter elements (luciferase or other reporter element) or a similar allele specific construct of the promoter (also possibly containing the exon 1+252C>G polymorphisms in linkage disequilibirum, Table 2) can be used as an assay to identify agents and test potential therapeutic methods to enhance or inhibit activity of the promoter region in an allele specific manner. Additionally, because NFKB1 −94delATTG has lower promoter activity than the −94insATTG and it has been shown by Ten et al. and others that NF-κB binding to the κB site 5' of nucleotide −61 (SEQ. ID NO:1) increases NFKB1 promoter activity, NFKB1 promoter activity can be specifically enhanced in individuals that contain the −94delATTG by stabilizing NF-κB protein binding to this −62 κB site. This construct can be used to differentially test binding enhancement based on the specific −94ins or del ATTG allele.

REFERENCES

Baldwin, A. S., Jr. Series Introduction: The transcription factor NF-B and human disease. JCI 2001; 107:3-6.

Bonen, D. K., Ogura, Y., Nicolae, D. L., Inohara, N., k Saab, L., Tanabke, T., Chen, F. F., Foster, S. J., Duerr, R. H., Brant, S. R., et al. (2003) Crohn's disease-associated NOD2 variants share a signaling defect in response to lipopolysaccharide and peptidoglycan. Gastroenterology, 124, 140-146.

Brant, S. R. and Okazaki, T. (2003) The genetics of IBD. In Bernstein, C. N. (ed.), The Inflammatory Bowel Disease Yearbook, Remedica, London, pp. 79-128.

De la Concha, E. G., Fernandez-Arquerio, M., Lopez-Nava, G., Martin E., Allcock, R. J., Conejero, L., Paredes, J. G. and Diaz-Rubio, M. (2000) Susceptibility to severe ulcerative colitis is associated with polymorphism in the central MHC gene IKBL, Gastroenterology, 119, 1491-1495.

Erdman, S., Fox, J. G., Dangler, C. A., Feldman, D., and Horwitz, B. H. (2001) Typhlocolities in NF-kappa B-deficient mice, J. Immunol., 166, 1443-1447.

Grentzmann, G., Ingram, J. A., Kelly, P. J., Gesteland, R. F. and Atkins, J. F. (1998) A dual-luciferase reporter system for studying recoding signals. RNA, 4, 479-486.

Hampe, J., Schreiber, S., Shaw, S. H., Lau, K. F., Bridger, S., MacPherson, A. J., Cardon, L. R., Sakul, H., Harris, T. J., Bucker, A. et al. (1999) A genomewide analysis provides evidence for novel linkages in inflammatory bowel disease in a large European cohort. Am. J. Hum. Genet., 64, 808-816.

Hisamatsu, T., Suzuki, M., Reinecker, H. C., Nadeau, W. J. McCormick, B. A. and Podolsky, D. K. (2003) CARD15/NOD2 functions as an antibacterial factor in human intestinal epithelial cells. Gastroenterology, 124, 993-1000.

Kruglyak, L., and Nickerson D. (2001) Variation is the spice of life, Nat. Genet., 27, 234-236.

Lake, S. L., Blacker, D. and Laird, N. M. (2000) Family-based tests of association in the presence of linkage. Am. J. Hum. Genet., 67, 1515-1525.

Miterski, N., Bohringer, S., Klein, W., Sindem, E., Haupts, M., Shimrigk, S. and Epplen, J. T. (2002) Inhibitors in the NFkappaB cascade comprise prime candidate genes predisposing to multiple sclerosis, especially in selected combinations. Genes Immun., 3, 211-219.

Ogura, Y., Bonen, D. K., Inohara, N., Nicolae, D. L., Chen, F. F., Ramos, R., frameshift mutation in NOD2 associated with susceptibility to Crohn's disease, Nature, 411, 603-606.

Rioux, J. D., Silberberg, M. S., Daly, M. J., Steinhart, A. H., McLeod, R. S., Griffith, A. M., Green, T., Brettin, T. S., Stone, V., Bull, S. B. et al (2000) Genomewide search in Canadian families with inflammatory bowel disease reveals two novel susceptibility loci. Am J. Hum. Genet., 66, 1863-1870.

Schreiber, S. Nikolaus, S. and Hampe, J. Activation of nuclear factor kappa B inflammatory bowel disease, Gut. 1998 April 42(4): 477-84

Sha, W. C., Liou H. C., Tuomanen E. I., and Baltimore D. (1995) Targeted disruption of the p50 subunit of NF-kappa B leads to multifocal defects in immune responses, Cell, 80, 321-330.

Spielman, R. S., McGinnis, R. E. and Ewens, W. J. (1993). Transmission test for linkage disequilibrium: the insulin gene region and insulin-dependent diabetes mellitus (IDDM), Am. J. Hum. Genet., 52, 506-516.

Ten, R. M., Paya, C. V., Israel, N., Le Bail, O., Mattei, M. B. Virelizier, J. L., Kkourilsky, P., Israel, A. The characterization of the promoter of the gene encoding the p50 subunit of NF-KB indicates that it participates in its own regulation. EMBO 1992; 11: 195-203.

Potter, J. J., Mezey, E., Cornelius, P., Crabb, D. W., Yang, V. W. the first 22 base pairs of the proximal promoter of the rat class I alcohol dehydrogenase gene is bipartite and interacts with multiple DNA binding proteins. Arch. Biochem Biophys. 1992 June; 295(2):360-8.

Standke, G. J. R., Meier, V. S., Groner, B. Mammary gland factor activated by Prolactin in mammary epithelial cells and acute-phase response factor activated by interleukin-6 in liver cells share DNA binding and Transactivation potential. Molecular Endocrinology 8(4) 469-477 1994

Waxman, D. J., Ram, P. A., Park, S. Choi, H. K. Intermittent plasma growth hormone triggers tyrosine phosphorylation and nuclear translocation of liver-expressed, Stat 5-related DNA binding protein. J. Biol. Chem. 270(22) 13262-13270, 1995.

Wintermeyer, P., Riess, O., Schols, L., Przuntek, H., Miterski, B., Epplen, J. T. and Kruger, R. (2002) Mutation analysis and association studies of nuclear factor-kappaB1 in sporadic Parkinson's disease patients, J. Neural Transm., 109, 1181-1188.

Karban and Okazaki, 2004

What is claimed is:

1. A method for identifying a human subject at increased risk for developing ulcerative colitis, comprising detecting the presence of a −94del ATTG allele in the NFKB1 gene promoter in a biological sample of said subject, wherein homozygosity of the −94del ATTG allele is indicative of an increased risk to develop ulcerative colitis compared with a subject having a −94ins ATTG allele.

2. The method of claim 1 wherein the subject at increased risk for developing ulcerative colitis is genetically related to a subject exhibiting symptoms of ulcerative colitis.

3. The method of claim 2 wherein the subject at risk to develop ulcerative colitis is genetically related to a second subject exhibiting ulcerative colitis.

4. A method for determining the presence of a −94del ATTG polymorphism in a human subject homozygous or heterozygous for the polymorphism, comprising amplifying genomic DNA with a first set of primers and a second set of primers to produce an amplified product, wherein the first set of primers comprise a first primer consisting of SEQ ID NO:12 and a second primer consisting of SEQ ID NO:13, and the second set of primers comprise a first primer consisting of SEQ ID NO:14 and a second primer consisting of SEQ ID NO:15, wherein the primers bracket position −91 to −94 in the NFKB1 gene promoter, and wherein the sequences of the amplified product are compared to SEQ ID NO: 1 to identify the −94del ATTG polymorphism.

* * * * *

SEQUENCE LISTING

<160> NUMBER OF SEQ ID NOS: 87

<210> SEQ ID NO 1
<211> LENGTH: 983
<212> TYPE: DNA
<213> ORGANISM: Homo sapiens

<400> SEQUENCE: 1

| | | | | | |
|---|---|---|---|---|---|
| ttttcagttg | tcactccacc | cagtagtgaa | acaatgagct | ctaaaatata | tatttcggct | 60 |
| caagctttct | tatgtgggga | ggtaatccac | ccgaaggtat | ccccagcctg | tacctaatac | 120 |
| agtgcccagc | actaaagcag | ctcagatgcc | agtgaatggt | ggccactggg | aggcctgtca | 180 |
| gtgggtgcca | gtagcggtct | cttcagagaa | aaagaaaact | ccctctgcc | agatcagtat | 240 |
| tttatgagct | gtgaaccaaa | accattgcta | ccaccatcac | tataattcta | tccacagtaa | 300 |
| ttatcataaa | ggcctaacaa | tgccttgtag | atgaacattc | tgagtaactg | ctctataacc | 360 |
| aggagattta | agaccgcacc | aaaaaccagt | agagggttat | actttactgg | gcacaagtcg | 420 |
| tttatgataa | cgaaattgta | gtttaatctg | tgaagagatg | tgaatgtaac | tgagacacgc | 480 |
| taaatggaat | atacagatga | gctttatttt | tatatctggc | atgcttggat | ccatgccgac | 540 |
| cctccagctg | ctcgggcctg | cccttagggg | ctatggacgc | atgactctat | cagcggcact | 600 |
| gccaccgccg | ccgcctccgt | gctgcctgcg | ttccccgacc | attgattggg | cccggcaggc | 660 |
| gcttcctggg | ggcttcccta | ccggctccag | cccttgggat | tcgggagcgc | cctgctagga | 720 |
| agccagagcc | ccgcaggggc | cgcggcgtcc | aggccgccta | acgcgcgccc | ctcgcccggc | 780 |
| gccccgaagc | ggccccgagg | ggcgggagcc | gaggcgagcg | gcaaggccgg | gccggggggcg | 840 |
| cacagcgccc | ctagaagtgc | gggcttcccc | caccccggc | agcgaccta | cctcccgccc | 900 |
| ccgctgcgtg | cgcgcgtgtg | tccgtctgtc | tgtatgctct | ctcgacgtca | gtgggaattt | 960 |
| ccagccagga | agtgagagag | tga | | | | 983 |

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
ccgggcccaa tcaatggtcg gg                                              22

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
ccgggcccaa tggtcggg                                                   18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 4
gccgggccca atggtcgggg                                              20

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cgggcccaat ggtcg                                                   15

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tccagaaaaa cactccacca                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
accttcgggt ggattacctc                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttcagttgtc actccaccca                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggtggtagca atggttttgg                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
```
aaagaaaact cccctctgcc                                                    20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttccatttaa gcgtgtctca g                                                  21

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttaatctgt gaagagatgt gaatg                                              25

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtagggaagc ccccagga                                                      18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcccttaggg gctatgga                                                      18

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctctggcttc ctagcaggg                                                     19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gttccccgac cattgattg                                                     19

```
<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aagcccgcac ttctaggg                                                 18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttcagttgtc actccaccca                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctctctcact tcctggctgg                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcgagcttaa cacgagggta                                               20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtgtgaaagc gggtgtaagt t                                             21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acgtaaacgt tgtccaaccc                                               20
```

```
<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaaccataca aggggtaatt gaga                                          24

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgccatcacc tttcaacaaa                                               20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgaggctcag gacagtgtga                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tacggagccc tctttcacag                                               20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaaggcaacc cgtactcatt                                               20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgtttccatg ttgctggaga                                               20

<210> SEQ ID NO 29
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gagggtctca gaaaggtccc                                                 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aatgcatgta gccccaagag                                                 20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gatgaaaacc aaagcctgga                                                 20

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ttgggcttta taaaagcatg g                                               21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctggacatca acctttcaag c                                               21

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttggtcatgt gtgctaaggg                                                 20

<210> SEQ ID NO 35
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 35
gcagcagagg gatgtttctt                                                   20

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gactgaacct tttgatcttg ttttt                                             25

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gagacaggag gatccctcaa                                                   20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctccaggaca cggtgttttt                                                   20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ctgtttgagg ccaggagttc                                                   20

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aacgcttctt gaaatttacc atc                                               23

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 41
tcatagccac tcaactcaca ga                                              22

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtcctgtcac accaaaggct                                                 20

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tgcattcatc aattatttgt caaga                                           25

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44 ttttctttc cttttgcagc                                                  20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tgcttttcca aaggcataca                                                 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tccttaagca tgccataccc                                                 20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 47
ttccaacaga tgacagcagc                                              20

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ttcaaaacat tttagggcca a                                            21

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
caaaggtttg tttttgtttt tgc                                          23

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cagtatggcc ccacctattg                                              20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
agcacttttg ggtgcaaatc                                              20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tttactgtcc ctccccatga                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53

-continued

```
aagttgggtt tgcattcctg                                          20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
atccaggaga ttgcctcaag                                          20

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aaaggcatgt tctttgggg                                           19

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
acattagggt accaggccc                                           19

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aacggggaaa atctgaaggt                                          20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
agccgaaaca ggaaacttga                                          20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59 ccaggggta gagagacaca                                           20
```

```
<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
catgagcttt ttagagcccg                                                   20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tgctgtggtc agaaggaatg                                                   20

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 62
agttgagggg actttcccag gc                                                22

<210> SEQ ID NO 63
<211> LENGTH: 8
<212> TYPE: DNA
<213> ORGANISM: Artificial Sequence
<220> FEATURE:
<223> OTHER INFORMATION: Description of Artificial Sequence:
      Illustrative transcription factor

<400> SEQUENCE: 63 gaccattg                                                                 8

<210> SEQ ID NO 64
<211> LENGTH: 6
<212> TYPE: DNA
<213> ORGANISM: Artificial Sequence
<220> FEATURE:
<223> OTHER INFORMATION: Description of Artificial Sequence:
      Illustrative transcription factor

<400> SEQUENCE: 64 accatt                                                                   6

<210> SEQ ID NO 65
<211> LENGTH: 9
<212> TYPE: DNA
<213> ORGANISM: Artificial Sequence
<220> FEATURE:
<223> OTHER INFORMATION: Description of Artificial Sequence:
      Illustrative transcription factor

<400> SEQUENCE: 65 ccattgatt                                                                9

<210> SEQ ID NO 66
```

```
<211> LENGTH: 9
<212> TYPE: DNA
<213> ORGANISM: Artificial Sequence
<220> FEATURE:
<223> OTHER INFORMATION: Description of Artificial Sequence:
      Illustrative transcription factor

<400> SEQUENCE: 66 cattgattg                                                                  9

<210> SEQ ID NO 67
<211> LENGTH: 10
<212> TYPE: DNA
<213> ORGANISM: Artificial Sequence
<220> FEATURE:
<223> OTHER INFORMATION: Description of Artificial Sequence:
      Illustrative transcription factor

<400> SEQUENCE: 67
cattgattgg                                                                10

<210> SEQ ID NO 68
<211> LENGTH: 8
<212> TYPE: DNA
<213> ORGANISM: Artificial Sequence
<220> FEATURE:
<223> OTHER INFORMATION: Description of Artificial Sequence:
      Illustrative transcription factor

<400> SEQUENCE: 68 attgattg                                                                   8

<210> SEQ ID NO 69
<211> LENGTH: 7
<212> TYPE: DNA
<213> ORGANISM: Artificial Sequence
<220> FEATURE:
<223> OTHER INFORMATION: Description of Artificial Sequence:
      Illustrative transcription factor

<400> SEQUENCE: 69 attgatt                                                                    7

<210> SEQ ID NO 70
<211> LENGTH: 7
<212> TYPE: DNA
<213> ORGANISM: Artificial Sequence
<220> FEATURE:
<223> OTHER INFORMATION: Description of Artificial Sequence:
      Illustrative transcription factor

<400> SEQUENCE: 70 ttgattg                                                                    7

<210> SEQ ID NO 71
<211> LENGTH: 6
<212> TYPE: DNA
<213> ORGANISM: Artificial Sequence
<220> FEATURE:
<223> OTHER INFORMATION: Description of Artificial Sequence:
      Illustrative transcription factor

<400> SEQUENCE: 71 tgattg                                                                     6

<210> SEQ ID NO 72
<211> LENGTH: 5
<212> TYPE: DNA
```

```
<213> ORGANISM: Artificial Sequence
<220> FEATURE:
<223> OTHER INFORMATION: Description of Artificial Sequence:
      Illustrative transcription factor

<400> SEQUENCE: 72 tgatt                                                                  5

<210> SEQ ID NO 73
<211> LENGTH: 6
<212> TYPE: DNA
<213> ORGANISM: Artificial Sequence
<220> FEATURE:
<223> OTHER INFORMATION: Description of Artificial Sequence:
      Illustrative transcription factor

<400> SEQUENCE: 73 tgattg                                                                 6

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence:
      Illustrative oligonucleotide

<400> SEQUENCE: 74
cccgaccatt gattgggccc gg                                              22

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence:
      Illustrative oligonucleotide

<400> SEQUENCE: 75
cccgaccatt gggcccgg                                                   18

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence:
      Illustrative oligonucleotide

<400> SEQUENCE: 76
ccgacccagt attgggcccg g                                               21

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence:
      Illustrative oligonucleotide

<400> SEQUENCE: 77
cccgaccatt gcagtggccc gg                                              22

<210> SEQ ID NO 78
<211> LENGTH: 22
<212> TYPE: DNA
<213> ORGANISM: Artificial Sequence
<220> FEATURE:
```

-continued

```
<223> OTHER INFORMATION: Description of Artificial Sequence:
      Illustrative oligonucleotide

<400> SEQUENCE: 78
cccgaccatt gaatgggccc gg                                              22

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence:
      Illustrative oligonucleotide

<400> SEQUENCE: 79
tccccgacca ttgggcccgg ca                                              22

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence:
      Illustrative oligonucleotide

<400> SEQUENCE: 80
cgaccattga ttgggcccgg                                                 20

<210> SEQ ID NO 81
<211> LENGTH: 16
<212> TYPE: DNA
<213> ORGANISM: Artificial Sequence
<220> FEATURE:
<223> OTHER INFORMATION: Description of Artificial Sequence:
      Illustrative oligonucleotide

<400> SEQUENCE: 81
cgaccattgg gcccgg                                                     16

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence:
      Illustrative oligonucleotide
<220> FEATURE:
<221> NAME/KEY: modified_base
<222> LOCATION: (14)
<223> OTHER INFORMATION: a, t, c, g, other or unknown
<220> FEATURE:
<221> NAME/KEY: modified_base
<222> LOCATION: (16)
<223> OTHER INFORMATION: a, t, c, g, other or unknown
<220> FEATURE:
<221> NAME/KEY: modified_base
<222> LOCATION: (18)
<223> OTHER INFORMATION: a, t, c, g, other or unknown

<400> SEQUENCE: 82
cgaccattga ttgngncngg                                                 20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence:
      Illustrative oligonucleotide
<220> FEATURE:
```

```
<221> NAME/KEY: modified_base
<222> LOCATION: (14)
<223> OTHER INFORMATION: a, t, c, g, other or unknown
<220> FEATURE:
<221> NAME/KEY: modified_base
<222> LOCATION: (16)
<223> OTHER INFORMATION: a, t, c, g, other or unknown
<220> FEATURE:
<221> NAME/KEY: modified_base
<222> LOCATION: (18)
<223> OTHER INFORMATION: a, t, c, g, other or unknown

<400> SEQUENCE: 83
cgaccattgg ggcngncngg                                           20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence:
      Illustrative oligonucleotide

<400> SEQUENCE: 84
cgaccattga ttgggcccgg                                           20

<210> SEQ ID NO 85
<211> LENGTH: 16
<212> TYPE: DNA
<213> ORGANISM: Artificial Sequence
<220> FEATURE:
<223> OTHER INFORMATION: Description of Artificial Sequence:
      Illustrative oligonucleotide

<400> SEQUENCE: 85
cgaccattgg gcccgg                                               16

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence:
      Illustrative oligonucleotide

<400> SEQUENCE: 86
cgaccattga ttgggcccgg                                           20

<210> SEQ ID NO 87
<211> LENGTH: 16
<212> TYPE: DNA
<213> ORGANISM: Artificial Sequence
<220> FEATURE:
<223> OTHER INFORMATION: Description of Artificial Sequence:
      Illustrative oligonucleotide

<400> SEQUENCE: 87
cgaccattgg gcccgg                                               16
```